US006403763B1

(12) United States Patent
Lowe

(10) Patent No.: US 6,403,763 B1
(45) Date of Patent: Jun. 11, 2002

(54) CHIRAL PEPTIDE NUCLEIC ACIDS

(75) Inventor: Gordon Lowe, Oxon (GB)

(73) Assignee: ISIS Innovation Limited (GB)

( * ) Notice: Subject to any disclaimer, the term of this patent is extended or adjusted under 35 U.S.C. 154(b) by 0 days.

(21) Appl. No.: 09/284,179

(22) PCT Filed: Oct. 13, 1997

(86) PCT No.: PCT/GB97/02820

§ 371 Date: Apr. 9, 1999

§ 102(e) Date: Apr. 9, 1999

(87) PCT Pub. No.: WO98/16550

PCT Pub. Date: Apr. 23, 1998

(30) Foreign Application Priority Data

Oct. 14, 1996 (GB) .................................................. 9621367

(51) Int. Cl.[7] .............................. A61K 38/00; C07K 1/00; C12Q 1/68; C07H 21/00
(52) U.S. Cl. .............................. 530/300; 435/6; 530/300; 536/22.1
(58) Field of Search ................................. 435/6; 536/22.1; 530/300, 350; 514/44

(56) References Cited

U.S. PATENT DOCUMENTS

| 4,501,901 | * | 2/1985 | Thottathil et al. | .................... 548/532 |
| 5,401,901 | | 3/1995 | Gerry et al. | ........................... 174/35 |
| 5,623,049 | * | 4/1997 | Löbberding et al. | ................. 530/300 |

FOREIGN PATENT DOCUMENTS

| 2131760 | 3/1995 | (CA) | ........................... C07K/007/04 |
| 0095584 | 12/1983 | (EP) | ............................. C07D/403/12 |
| 0646596 | 4/1995 | (EP) | .................................. C07K/5/00 |

* cited by examiner

Primary Examiner—Ardin H. Marschel
(74) Attorney, Agent, or Firm—Volpe & Koenig, P.C.

(57) ABSTRACT

Chiral peptide nucleic acids are provided which hybridize strongly with complementary nucleic acids and have potential as antigene and antisense agents and as tools in molecular biology.

18 Claims, 3 Drawing Sheets

CHIRAL PEPTIDE NUCLEIC ACIDS

This application is a filing under 35 U.S.C. Å 371 of PCT/GB97/02820, filed Oct. 13, 1997.

This invention describes the synthesis and properties of a ovel class of chiral peptide nucleic acids (cPNAs) which hybridise strongly with complementary nucleic acids. As such they have potential as antigene and antisense agents and as tools in molecular biology.

Oligonucleotides are potentially useful for the regulation of genetic expression by binding with DNA or mRNA[1]. However, natural oligonucleotides are degraded by nucleases, consequently there is considerable interest in synthetic oligonudeotide analogues which are stable under physiological conditions. Recently, there has been interest in oligonucleotide analogues in which the sugar-phosphate backbone is replaced by a peptide chain[2] after the success of the so-called Peptide Nucleic Acids (PNA)[3], but more correctly referred to as Polyamide Nucleic Acids[4].

The sugar phosphate backbone of a nucleic acid consists of a repeating unit of six atoms, configurationally and conformationally constrained by the Dribose or 2'-deoxy-D-ribose ring. If this could be replaced by a dipeptide unit the new backbone would be amenable to preparation by solid phase peptide synthesis. Molecular modelling by computer graphics suggested that a peptide chain consisting of an alternate sequence of a "nucleo-amino acid" derived from proline and a "spacer amino acid", which could be any amino acid, should be a suitable structural analogue of the ribose phosphate backbone of nucleic acids as shown.

(a)
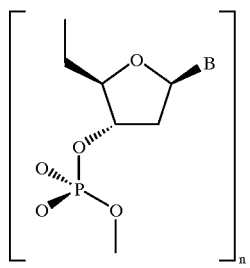

(b)
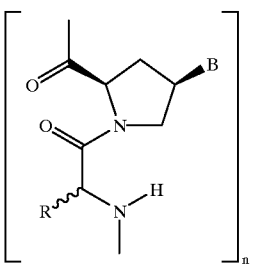

SUMMARY OF INVENTION

This invention provides compounds of formula (I)

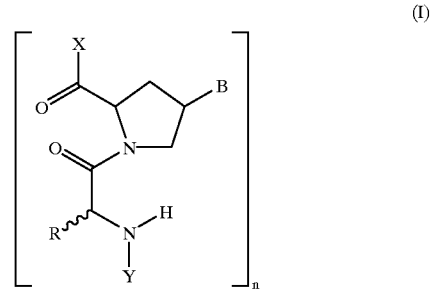

(I)

where n is 1 or 2–200

B is a protected or unprotected heterocyclic base capable of Watson-Crick or of Hoogsteen pairing, R is H, C1–C12 alkyl, C6–C12 aralkyl or C6–C12 heteroaryl which may carry one or more subsftuents preferably selected from hydroxyl, carboxyl, amine, amide, thiol, thioether or phenol, X is OH or OR' where R' is a protecting group or an activating group or a lipophilic group or an amino acid or amino amide or nucleoside, Y is H or a protecting group or a lipophilic group or an amino acyl group or nudeoside.

When n is 1, these compounds are peptide nucleotide analogues. When n is 2 to about 30 these compounds are peptide oligonucleotides, which are synthesised as described below and can be s hybridised to ordinary oligo or poly-nucleotides. Typically the two strands are hybridised to one another in a 1:1 molar ratio by basespecific Watson-Crick base pairing.

B is a base capable of Watsonrick or of Hoogsteen pairing. This may be a naturally occurring nudeobase selected from A,C,G,T and U; or a base analogue that may be base specific or degenerate, e.g. by having the ability to base pair with both pyrimidines (T/C) or both purines (A/G) or universal, by forming base pairs with each of the natural bases without discrimination. Many such base analogues are known, e.g. hypoxanthene, 3-nitropyrrole, 5-nitroindole, and those cited by Lin and Brown[5] and all are envisaged for use in the present invention.

The compounds of formula (I) contain proline of undefined stereochemistry. Although compounds with the trans-stereochemistry may have interesting properties, compounds with the cis-stereochemistry are preferred either with the Dcnfiguration as shown in (II) or the L-configuration shown in structure (III). In these compounds both stereoisomers of the "spacer amino acid" NHCHRCO are envisaged.

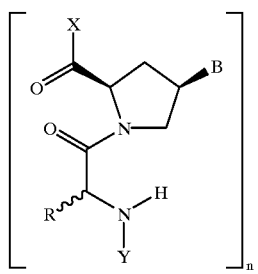

(II)

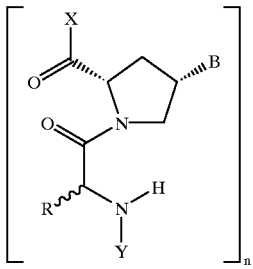

(III)

Provided that it does not sterically hinder chain extension of hybridisation, the group R could have diverse structures. The group, however, can be chosen to confer desired hydrophobic, hydrophilic and/or electrostatic properties on the molecule. When the group R is other than H it generates a chiral centre and the two stereoisomers may allow for discrimination in the hybridisation of DNA and RNA. When the amino acid (—NH—CHR—CO) is a naturally occurring amino acid, then the amino acid should be readily and cheaply available as a building block for compounds of this invention. Any of the natural or unnatural α-amino acids could be used e.g. glycine. or L- or D-serine or lysine. The nature of X can be varied from the negatively charged carboxylate ion (X=O) to the incorporation of a positively charged lysine residue. Examples of the latter are provided in the experimental section and can be used to prevent aggregation and to assist hybridisation to the negatively charged oligonucleotides. Y will most commonly be H but could be any group which might be useful to improve the physical or biological properties of the material.

Any one of B, R, X and Y may include a signal moiety, which may be for example a radioisotope, an isotope detectable by mass spectrometry or NMR, a hapten, a fluorescent group or a component of a chemiluminescent or fluorescent or chromogenic enzyme system. The signal moiety may be joined to the peptide nudeotide analogue either directly or through a linker chain of up to 30 atoms as well known in the field.

In another aspect the invention provides a method of making the peptide nucleotide analogue of formula (I), comprising the steps of:

a) reacting an N-protected C-protected 4-hydroxy proline with a base selected from Nprotected thymine, $N_6$-protected adenine, $N_4$-protected cytosine, $N_2$—$O_6$-protected guanine and $N_3$-protected uracil.

b) deprotecting the proline amino group of the product of a), c) reacting the product of b) with an N-protected amino acid, d) optionally removing protecting groups from the product of c).

In another aspect the invention provides a method of converting a peptide nucleotide analogue of formula (I) in which n is 1 into a peptide oligonucdeotide of formula (I) in which n is 2–200, comprising the steps of:

i) providing a support carrying primary amine groups, ii) coupling an N-protected peptide nucleotide analogue of formula (I) to the support, iii) removing the N-terminal protecting group, iv) coupling an Nprotected nucdeotide analogue of formula (I) to the thus-derivatised support, v) repeating steps iii) and iv) one or more times, and vi) optionally removing the resulting peptide oligonucleotide from the support.

The invention also provides a compound of formula (IV)

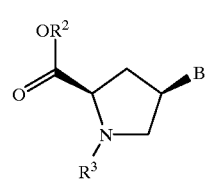

(IV)

where $R^2$ is H or a protecting group,
$R^3$ is H or a protecting group compatible with $R^2$, and
B is a protected or unprotected heterocyclic base.
The invention also provides a compound of formula (V)

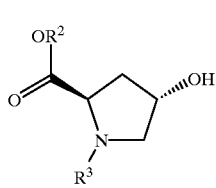

(V)

where $R^2$ is diphenylmethyl, and
$R^3$ is t-butoxycarbonyl.

DETAILED DESCRIPTION

The (2R,4R) ("cis-D")-proline was chosen since this is analogous to the stereochemistry of deoxyribonucleotides. The lack of negative charge on the peptide backbone would be expected to lead to a higher affinity for complementary oligonucleotide sequences in nudeic acids. Moreover these novel peptide nucleic adds can also be modified easily by using different "spacer amino acids" to affect physical and biological properties such as solubility, cell permeability, etc. in order to achieve higher therapeutic activity. Such peptide nucleic acids should be stable to proteases since they contain substituted D-proline residues at alternate sites. Since coupling to secondary amino acids can be slow and inefficient, it was decided to use dipeptide building blocks in which the amino-acylprorine bond is formed in solution as in dipeptide (1). In the alternative arrangement, ire. polyiamino acid, there is likely to be a serious problem of racemisation during the coupling if the amino acid is chiral, whereas such racemisation is not expected when the Gterminus of the activated fragment is proline because N-acylprolines can not racemise by the oxazolone mechanism[6].

Because of the mild conditions used for the deprotection of the N-Fmoc group, the Fmoc/O$^t$Bu strategy in solid phase peptde synthesis is favoured over the classical Boc/OBzl strategy[7]. Furthermore, most machine synthesisers capable of handling small scale synthesis (50 μmol or less) can accommodate only the Fmoc/O$^t$Bu strategy. For these reasons, it was decided to use the Fmoc instead of Boc as the N-protecting group.

There were two possible synthetic pathways to the target dipeptide (1), the two amino acids may be coupled first and the nucleobase attached later by the Mitsunobu reaction or the nucleobase may be incorporated before the peptide coupling. The first approach has the advantage of being a more convergent approach. However, a preliminary investigation suggested that it is not satisfactory because of the extensive cleavage of the Fmoc group during the Mitsunobu reaction. It also seemed likely that displacement of tosylate by a nucleobase would give similar premature cleavage of the Fmoc group since the reactions require basic conditions.

A temporary N-protecting group for the hydroxyproline was required, therefore, which is stable to the basic conditions of the Mitsunobu reaction but which can be removed, without disturbing the carboxyl protecting group, in order to allow coupling with Fmoc-glycine (or other amino acid) to give the Fmoc-dipeptide (1). As the carboxyl protecting group must be selectively removed in the presence of the Fmoc group at the end of the synthesis, an acidabile protecting group seemed appropriate. The combination of the acid labile Boc group and diphenylmethyl (Dpm) ester is ideal because introduction and cleavage of both groups are simple and high yielding. The Dpm ester is fully compatible with the N-Fmoc group and a selective cleavage of a Boc group in the presence of a diphenylmethyl ester is possible[8].

Initial studies were undertaken with the commercially available trans-4-hydroxy-L-proline, which was protected as its N-Boc/Dpm ester derivative according to the method described by Tozuka and Takaya[9]. The crystalline derivative (2a) was obtained in greater than 80% yield in two steps.

The Mitsunobu reaction on (2a) with N$_3$-benzoylthymine (BzT) gave the thymine derivative (3a), together with a less polar product, possibly the O$_2$-isomer or the elimination product. Fortunately, the thymine derivative (3a) is crystalline and after column chromatography and one recrystallisation, the pure material was obtained in 51% yield.

Deprotection of the N-Boc group of the protected thymine derivative (3a) was accomplished with methanolic HCl. The resulting amine salt was reacted with Fmoc-glycne pentafluorophenyl ester in the presence of diisopropylethylamine (DIEA) to give the protected dipeptide (4a) in excellent yield. Treatment of (4a) with trifluoroacetic acid, either as a neat liquid or in the presence of phenol or anisole as a scavenger,[10] at room temperature for a few hours led to the formation of roughly equal amounts of two products as shown by tic and hplc, which could not be separated by crystallisation. The unexpected product, which was more polar than the desired product, was identified as the debenzoylated thymine derivative (5a). Since protection of thymine at N$_3$ was only required for selective alkylation at thymine-N$_1$, the debenzoylated thymine derivative (5a) was suitable for oligomer synthesis. However, attempts to completely remove the benzoyl group by prolonged treatment with trifluoroacetic acid resulted in a complex mixture. HBr in acetic acid gave better results. Brief treatment of the mixture of products from trifluoroacetic acid cleavage with 10% HBr in acetic acid resulted in a complete cleavage of the benzoyl group as shown by hplc. The cleavage conditions have also been applied to the fully protected dipeptide (4a) without pretreatment with trifluoroacetic acid with equal success. The synthesis of Fmoc-dipeptide bearing thymine at 4-position in the CiS-L proline series is summarised in Scheme 1.

The protected cis- and trans-hydroxymproline (2b) and (2c) were required for the preparation of the trans- and cis-D-proline dipeptides bearing nucleobases. The reaction of N-Boc-cis-4-hydroxy-D-proline with diphenyldiazomethane gave the Dpm ester (2b) in 90% yield. Inversion of the 4-OH group in (2b) to give (2c) was effected by the Mitsunobu reaction. By this route, (2c) was prepared in multigram quantities from (2b) in excellent yield (90%, 2 steps) (Scheme 2). The specific rotation of the (2c) ($[\alpha]_D^5$+ 53.0, c=1.0, EtOH) when compared to that of the trans-L isomer ($[\alpha]_D^{25}$−54.3, c=1.0, EtOH) indicated that inversion was essentially complete.

The Mitsunobu reaction on the diastereomers, (2b) and (2c), with N$_3$-benzoylthymine on a 20 mmol scale gave the products (3b) and (3c) in 33 and 36% yield respectively. The Boc group in (3b) and (3c) was removed with methanolic HCl and the products treated with Fmoc-glycine pentafluorophenyl ester to give the protected dipeptides (4b) and (4c). After treatment with 10% HBr in acetic acid the Fmoc-dipeptide acids (5b) and (5c) were obtained with concomitant cleavage of the N$_3$-benzoyl group. The intermediate protected dipepfide (4b) and the final product (Sb) were not crystallised as readily as their diastereomers (4c) and (5c). However, the purity of the crude Fmoc-dipeptide (5b) and (5c) was proved to be satisfactory by hplc.

The Fmoc-dipeptide (6a), (5b) and (5c) were prepared in gramquantities for solid phase synthesis. Pentafluorophenyl esters of the diastereomeric thymine dipeptides (6a), (6b) and (6c) were all prepared by reactions of the free acids with pentafluorophenol in the presence of DCCl in dichloromethane.[11] These active esters were crystalline solids which were stable enough to permit purification by silica gel column chromatography and could be stored for several months at −20° C. without apparent decomposition according to $^1$H nmr.

Binding studies between the 10 mers derived from coupling of (6a), (6b) and (6c), and poly(dA), showed that the oligomer derived from (6c) binds most strongly. The Cis-D proline series was selected therefore for further investigation. The protected cis-hydroxy-D-proline (2b) was converted into the crystalline trans-D-tosylate (7) in 68% yield by a Mitsunobu reaction with methyl p-toluenesulfonate in the presence of triphenylphosphine and DEAD, according to the method of Peterson and Vince.[12] Reactions of (7) and N$_6$-benzoyladenine in the presence of K$_2$CO$_3$ and a catalytic amount of 18crown-6 in DMF afforded the N$_9$-isomer of Boc-D-Pro(cis-4-BzA)-ODpm (8) in 42% yield. However, on scaling up, a small amount of another isomer (~5%) was also isolated. This was probably the N$_7$-isomer according to the upfield $^{13}$C chemical shift of adenine C$_5$ (115.0 and 114.6 ppm, rotamers) relative to the major product (123.4 ppm)[13].

Deprotection of the Boc group in (8) was first attempted by methanolic HCl as described previously for the thymine derivatives, however, less selectivity was achieved. However, p-toluenesulfonic acid in acetonitrile, which has been successfully applied to deprotect the N-Boc group during the synthesis of cephalosporin derivatives,[14] cleanly removed the Boc group without cleaving the Dpm ester. The product was reacted with Fmoc-glycine pentafluorophenyl ester to gave the Fmoc-dipeptide diphenylmethyl ester (9) in 85% yield. Deprotection of the Dpm ester with trifluoroacetic acid in the presence of anisole gave the free acid which was directly converted into the pentafluorophenyl ester (10) by reacting with pentafluorophenol in the presence of DCCl. The $N_6$-benzoyl group on adenine remained intact throughout the reaction sequence. Attempted purification of the highly polar pentafluorophenyl ester (10) by column chromatography found only limited success. However, the crude product after trituration and washing with hexane, was shown by $^1H$ nmr to contain approximately 10% of dicyclohexylurea (DCU) as the only contaminant, and was used successfully for solid phase peptide synthesis.

Reaction of the trans-D-tosylate (7) with $N_4$-benzoylcytosine in the presence of $K_2CO_3$/18-crown-6 in DMF gave the desired $N_1$-isomer, Boc-D-Pro(cis-4-$N_1$-BzC)-ODpm, (11) in 25% yield along with the less polar $O_2$-isomer in 41% yield, which could be readily separated by chromatography on silica gel. The identity of the two isomers was further confirmed by the characteristic downfield shift of the $^{13}C$ resonance of $C_4$, of the $O_2$-isomer compared to the $NN_1$-isomer. Since $N_4$-benzoylcytosine was shown to be partially hydrolysed in hot 85% acetic acid to give uracil,[15] the stability of this group towards acids was tested before attempting deprotection of the Boc group or the diphenylmethyl ester. The Boc-protected amino acid (11) was treated with trifluoroacetic acid in the presence of anisole for 2 h. $^1H$ nmr of the product showed that the Boc and Dpm groups were completely removed whereas the benzoyl group was stable thus demonstrating that the deprotection conditions were satisfactory. Removal of the Boc group of (11) and reaction of the product with Fmoc-glycine pentafluorophenyl ester as described for the adenine analogue gave the protected cytosine dipeptide (12) in 70% overall yield.

The benzoylcytosine dipeptide and its pentafluorophenyl ester (13) were synthesised in essentially the same way as the thymine and adenine analogues.

The Mitsunobu reaction between $N_2$-isobutyryl-$O_6$(4'-nitrophenylethyl)guaninel[6] and the protected trans-4-hydroxy-D-proline (2c) gave the required product, but, could not be isolated free from diethyl hydrazinedicarboxylate. Treatment with DBU in pyridine to remove the $O_6$-nitrophenylethyl protecting group followed by column chromatography, however, gave the pure $N_9$-substfduted isobutyrylguanine derivative (14) as a white solid in 43% overall yield. Removal of the Boc group and reaction of the product with Fmoc-glycine pentafluorophenyl ester gave the protected guanine dipeptide (15) in 52% yield. Removal of the carboxyl protecting group and reaction of the product with pentafluorophenol and DCCl gave the isobutyrylguanine dipeptide and its pentafluorophenyl ester (16).

A model synthesis was first carried out manually on the trans-D-proline analogue. The target was a $T_{10}$ cPNA: H-[Gly-D-Pro(trans-4-T)]$_{10}$-Lys-$NH_2$. The lysine amide was included at the C-terminus to prevent self-aggregation and to increase water solubility. An acid-labile dimethoxybenzhydrylamine Novasyn-TGR resin was chosen as the solid support since cleavage with trifluoroacetic acid leads directly to the peptide amide. The polyethyleneglycol matrix also improves the swelling properties of the resin and allows better access of the reagents to the growing peptide chain. The first Wysine residue was introduced by coupling with Fmoc-Lys(Boc)OPfp in the presence of HOBt. The peptide was synthesised from Fmoc-Gly-D-Pro(trans-4-T)OH (5b), in the presence of HBTU/DIEA according to the standard protocol for Fmoc-solid phase synthesis.[17] The efficiency of the coupling reactions, which was followed quantitatively after deprotection of the Fmoc group by measuring the absorbance of the dibenzofulvene-piperidine adduct ($\epsilon_{264}$= 18000) liberated during deprotection, was not as good as expected despite the use of a large excess of reagents and prolonged reaction times.

Much better coupling was obtained by first converting (5b) into the pentafluorophenyl (Pfp) ester (6b) with DCCl and pentafluoro-phenol, and then performing the coupling in the presence of HOBt A possible reason for the low yield in the case of HBTU activation was that the activated monomer may have been lost by cyclisation to a diketopiperazine derivative. This is a very facile reaction for the active esters of protected or unprotected dipeptides which contain proline at the C-terrnini, especially in the presence of a base, for example, Z-Gly-Pro-ONp, is known to spontaneously cydise under basic conditions.[18] The pentafluorophenyl ester is less reactive than the O-acylisourea or HOBt ester formed during HBTU activation and the coupling does not require basic conditions, which probably explains the improved coupling.

The decathymine chiral peptide nucleic acids with different stereochemistry at proline (trans-D, cis-D and cis-L), i.e. H-[Gly-D-Pro(trans-4-T)]$_{10}$-Lys-$NH_2$, H-[Gly-D-Pro(cis-4-T)]$_{10}$-Lys-$NH_2$ and H-[Gly-L-Pro(cis-4-T)]$_{10}$-Lys-$NH_2$ were successfully prepared by successive coupling of the corresponding dipeptide pentafluorophenyl esters according to the protocol shown in Scheme 3 on 5 $\mu$mol scales. The syntheses were accomplished rapidly and efficiently. Total amounts of activated dipeptides required for each 5 $\mu$mol synthesis of a decamer were approximately 150 mg. The chiral peptide nucleic acids were released from the resin and purified according to the standard protocol. In each case, analytical hplc of the crude products showed that they were 90–95% pure.

The peptides were purified by reverse phase hplc and their identity confirmed by electrospray mass spectrometry (Table 1). Interestingly, these higher oligomers showed an ability to form adducts with alkali metal ions especially potassium in the mass spectrometer, as evidenced by the presence of mass peaks at M+39n, where n is an integral number, in addition to the expected molecular ion peak. In some cases, these potassium ion adducts appeared as the major peaks in the mass spectra. All the $T_{10}$ chiral peptide nucleic acids were sufficiently soluble in water for biological studies (>1 mg/mL at room temperature), although the trans-D-nanalogue was considerably more soluble than the other two.

Next the incorporation of different nucleobases into the chiral peptide nucleic acids was explored. The mixed adenine-thymine peptide nucleic acids of the transe and cis-L series were synthesised from the pentafluorophenyl esters without difficulty. However, attempts to remove the nucleobase protecting group (in this case, benzoyl) by treatment with aqueous ammonia under various conditions resulted in degradation of the peptide as shown by hplc. It seemed unlikely that the degradation resulted from direct hydrolysis or ammonolysis of the peptide bond, since the Gly-Pro and Pro-Gly bonds are stable to hot aqueous ammonia. Hplc and electrospray mass spectral analysis of the degradation products showed that they are the dipeptides Gly-Pro (or Pro-Gly) with the nucleobases remaining attached. This suggested that the degradation was probably caused by intramolecular attack by the amino group of the N-terminal glycine on the amide carbonyl of the next residue to release the bicyclic diketopiperazine, which could undergo further hydrolytic ring opening under the deprotection conditions to form the corresponding dipeptide observed in the mass spectrum. The process would be repeated until the entire peptide chain was degraded.

Understanding the mechanism of degradation made it possible to avoid this serious side reaction by modifying the N-terminus of the peptide nucleic acid in a way that would diminish the nucleophilicity of the amino groups. It was therefore decided to find another protecting group which could be removed under conditions compatible with the peptide, preferably without introducing additional steps. The Boc group was used as it is labile under the conditions for peptide cleavage from the resin but stable under the conditions necessary to deprotect the nucleobases on the solid support. This protection-deprotection scheme was tested by synthesizing two mixed A-T sequences H-[Gly-L-Pro(cis-4-T)]$_2$-[Gly-L-Pro(cis-4-A)-Gly-Prob(cis-4-T)]$_2$-Lys-NH$_2$ and H-[Gly-L-Pro(cis-4-T)]$_6$-[Gly-L-Pro(cis-4-A)-Gly-L-Pro (cis-4-T)]Lys-NH$_2$ The fully protected peptides were assembled on the solid support as usual and after the final removal of the N-Fmoc group, the free N-termini were capped with di-t-butyl dicarbonate (Boc$_2$O) in the presence of DIEA in DMF. A qualitative ninhydrn test indicated that the coupling was essentially complete. After flushing the reaction vessels with DMF, the resins were treated with 1:1 ethylenediamine-ethanol at room temperature overnight. This deprotection reagent has been used as a milder alternative to aqueous ammonia for the base labile methylphosphonate oligonucleotides.[19] The reagent was chosen here because the reaction could be carried out at room temperature and in the same vessel used for the peptide synthesis. Another advantage is that the resin swells better in this non-aqueous medium—swelling properties of the solid support are crucial for solid phase reactions. The relatively non-volatile ethylenediamine and benzamide derivative from the cleavage reactions were easily removed by flushing the reaction vessels with DMF. Final cleavage and purification were carried out according to the standard method. Reverse phase hplc analysis of the completely deprotected peptides showed dean single products in each case. The identity of the products was confirmed by mass spectrometry {H-[Gly-L-Pro(cis-4-T)]$_2$-[Gly-L-Pro(cis-4-A)-Gly-L-Pro (cis-4-T)]$_2$-Lys-NH$_2$: M$_r$ calcd. 1832.84, found 1832.40±0.10; H-[Gly-L-Pro(cis-4-T)]$_6$-[Gly-L-Pro(cis-4-A)-Gly-L-Pro(cis-4-T)]$_2$-Lys-NH$_2$: M$_r$ calcd. 2945.92, found 2945.32±14}.

The synthesis of chiral peptide nucleic acids incorporating all four natural nucleobases was undertaken next. The first model sequence synthesised was the tetramer H-Gly-D-Pro (cis-4-C)-Gly-D-Pro(cis-4-G)-Gly-D-Pro(cis-4-T)-Gly-D-Pro(cis-4-A)-Lys-NH$_2$. All the coupling was carried out under the conditions described for the oligothymine peptide nucleic acids. The coupling efficiency was monitored by measuring the absorbance of dibenzofulvene-piperidine adduct from the deprotection step and showed that the guanine and cytosine could be introduced efficiently (>90% coupling yield, single coupling). The N-terrninus of the resin bound peptide was then capped with the Boc group after removal of the last N-Fmoc group and then the resin was treated with concentrated aqueous ammonia-dioxane 1:1 at 55° C. overnight to remove the nucleobase protecting groups. Ethylenediamine was avoided in this instance because it had been shown to cause modification of the cytosine residue in oligonudeotides by displacement of the exocyclic amino group with the aminoethylamino group.[2] Final deprotection of the Boc group and cleavage from the solid support was carried out according to the standard protocol. Reverse phase hplc analysis revealed a single major product which was shown to be the desired product by electrospray mass spectrometry {H-Gly-D-Pro(cis-4-C)-Gly-D-Pro(cis-4-G)-Gly-D-Pro(cis-4-T)-Gly-D-Pro(cis-4-A)-Lys-NH$_2$: M$_r$ calcd. 1276.54, found 1277.00±0.07}.

A decamer mixed-base peptide nucleic acid, H-Gly-D-Pro (cis-4-G)-Gly-D-Pro(cis-4-T)-Gly-D-Pro(cis-4-A)-Gly-D-Pro(cis-4-G)-Gly-D-Pro(cis-4-A)-Gly-D-Pro(cis-4-T)Gly-D-Pro(cis-4-T)Gly-D-Pro(cis-4-A)-Gly-D-Pro(cis-4C)-Gly-D-Pro(cis-4-T)-Lys-NH$_2$, was also synthesised by the standard protocol giving the product (M$_r$ calcd. 2973.15, found 2974.80±0.35) in good yield and purity as judged by reverse phase hplc. The reverse phase hplc chromatogram and electrospray mass spectrum of the decamer are shown in FIG. 1 and FIG. 2.

Hybridization Studies

The deca-thymine glycyl-proline peptide nucleic acids with cis-L, trans-D and cis-D stereochemistry, and C-terminal L-lysinamide were mixed in 1:1 ratio with poly (rA) and poly(dA) in the presence of 150 mM NaCl and sodium phosphate buffer (10 mM Na$^+$, pH 7.0) and the T$_m$ determined (FIG. 3). The cis-D- and cis-L-PNAs, but not the trans-D-PNA showed well defined single-transition mewling curves with both poly(rA) and poly(dA). The magnitudes of absorbance change were of the order of 30–40%. The T$_m$ were as shown in Table 2.

The slightly higher T$_m$ for the chiral peptide nucleic acid.poly(rA) complexes suggests that they are slightly more stable than the peptide nudeic acid.poly(dA) complexes. Although both cis-D and cis-L analogues gave melting curves with poly(dA) and poly(rA), only the cis-D analogue gave a welldefined melting curve with (dA)$_{10}$, with T$_m$=61° C., under the same conditions. The cis-L analogue gave a broad melting curve with a T$_m$ near room temperature. These results suggest that there is a stronger interaction between the cis-D analogue, which possessed the same absolute stereochemistry as natural oligonucleotides.

Further investigation of the nature of the cis-D peptide nucleic acid-oligonucleotide interaction was undertaken by determining the melting curve with (dT)$_{10}$. The 1:1 mixture with (dT)$_{10}$ showed no significant increase in absorbance at 260 nm on heating whereas the 1:1 mixture with (DA)$_{10}$ showed strong hyperchromicity (ca. 20%) suggesting that the binding is probably specific for A.T pairs, presumably by Watson-Crick base pairing.

In order to determine the stoichiometry of the peptide nucleic acid-nucleic acid complexes, a titration experiment between cis-D-stereomer and poly(rA) was investigated. A well-defined mixing curve was obtained with minima at 1:1 ratio of peptide nucleic to nucleic acid in sodium phosphate buffer (10mM Na$^+$, pH 7.0) suggesting a 1:1 stoichiontetry (FIG. 4). A similar titration experiment with (dA)$_{10}$ under the same conditions gave essentially the same result.

All four bases found in DNA were introduced into the glycylproline building units with the cis-D configuration and from these mixed cPNAs containing all four nucleobases have been made. Sequence ID No. 1, GTAGATCACT, capped at its C-terminus with L-lysinamide was synthesised, and its binding properties with oligonucleotides investigated. Since it is important to determine the preferred orientation of binding of these novel cPNAs to oligonudeotides, both of the possible complementary oligonucleotides were prepared, i.e. 5'-CATCTAGTGA-3', Sequence ID No. 2, and 5'-AGTGATCTAC-3' Sequence ID No. 3, and hybridised with the chiral PNA. Their T$_m$ values were 47° C. and 43° C. respectively indicating that the N-terninus of the cPNA preferentially binds to the 5'-terminus of the oligonucleotide, and the C-terminus to the 3'-terminus of the oligonucleotide. This is known as the antiparallel mode of binding, but it is seen that the stability of the alternative parallel binding complex is only slightly less stable.

Following the promising results obtained on the binding studies of the cPNA with complementary oligonucleotides by $T_m$ measurement, a $^1$H NMR experiment was performed on the mixed sequence decamer, H-Gly-D-Pro(cis-4-G)-Gly-D-Pro(cis-4-T)-Gly-D-Pro(cis-4A)-Gly-D-Pro(cis-4-G)Gly-D-Pro(cis-4-A)-Gly-D-Pro(cis-4-T)-Gly-D-Pro(cis-4-C)-Gly-D-Pro(cis-4-A)-Gly-D-Pro(cis-4-C)-Gly-D-Pro (cis-4T)-LysNH$_2$, and its complementary oligonucleotides, both in parallel and antiparallel fashion. Unfortunately upon mixing the two components at the mmolar concentration required, a white precipitate formed immediately and no NMR signals could be observed apart from those of excess starting material. It is clear that even though the cPNA and the oligonucleotide alone are freely soluble in water, the complex formed between them is not at the high concentration required. In an attempt to overcome this problem it was decided to synthesise a cPNA analogue, containing a hydrophilic spacer amino acid—namely serine—in place of the glycine spacer in the backbone while retaining the cis-D-configuration of the proline moiety. As there are two enantiomers and our preliminary molecular model suggested that the stereochemistry of the spacer amino acid may have considerable effects on the binding strength of the resulting diastereomeric cPNAs with A- and B-forms of DNA, both enantiomers of serine were studied. Thus the target molecules were diastereomeric thymine-decamers H-[L-Ser-D-Pro(cis-4-T)]$_{10}$LysNH$_2$ ("LD-ST10") and H-[D-Ser-D-Pro(cis-4-T)]$_{10}$LysNH$_2$ ("DD-ST10").

The required Fmoc-protected dipeptide diastereoisomeric synthons (17) were synthesised from Boc-D-Pro(cis-4-N$^3$BzT)-Odpm (3c) in an analogous manner to the glycyl-proline analogue. The serine hydroxyl side chain was protected as a t-butyl ether as in the traditional Fmoc-O$^t$Bu orthogonal protection scheme. The Boc- group in the starting material was removed by p-TsOH in acetoninle as described previously, the amine tosylate was then reacted with Fmoc-Ser(OtBu)-OH in the presence of DCCl and HOBt in MeCN/DMF, after neutralisation with DIEA. Both enantiomers of serine gave similar yields (70–90%) of the desired protected dipeptides, Fmoc-L-Ser(O$^t$Bu)-D-Pr.(cis-4-BzT)-ODpm and Fmoc-D-Ser(O$^t$Bu)-D-Pro-(cis-4-BzT)-ODpm, which were isolated as white amorphous solids after column chromatography and were characterised by $^1$H, $^{13}$C NMR and APCIMS. Deprotection of the ODpm ester of Fmoc-L-Ser(O$^t$Bu)-D-Pro-(cis-4-BzT)-ODpm was found to be problematic since catalytic transfer hydrogenolysis using different hydrogen donors including ammonium formate, formic acid and cyclohexene and catalysts—Pd black, 10% Pd/C, and freshly prepared 5% Pd/BaSO$_4$, gave unsatisfactory results. Aadic conditions were an alterative, if selectivity between the Dpm ester and t-Bu ether could be achieved. Various combinations were attempted, but 4M HCl in dioxane appeared to give the best result. The deprotected material, consisting a mixture of the desired Fmoc-dipeptide acid and some debutylated product was subjected to a reaction with pentafluorophenol/DCCl to give the final active ester of the Fmoc-dipeptide, which could be purified by column chromatography on silica gel (Scheme 4). The final products were obtained in a pure form and were characterised by $^1$H NMR and APCI-MS. It should be noted that the benzoyl protecting group on the thymine ring remained intact throughout the reaction sequence but this should not be a problem since this benzoyl group is removed readily upon treatment with 20% piperidine in DMF during deprotection of the Fmoc group in the solid phase synthesis step.

Solid phase synthesis of the two cPNA decamers, LD-ST10 and DD-ST10, were carried out according to our standard protocol on a 5 μmol scale and the efficiency of each coupling step was monitored by measuring the absorbance of the dibenzofulvene-piperidine adduct released from deprotection of the Fmoc group and this showed that the coupling proceeded efficiently (95–100%). Both cPNA diastereomers could be purified to give the pure 10-mers by HPLC which gave correct masses by ESI-MS (3266, M–H+ K, identical spectra for both isomers). The purified cPNAs, LD-ST10 and DD-ST10, were obtained in 28 and 16% yield respectively. Both of the serine-containing cPNAs were freely soluble in water at a concentration of 2 mM.

A $^1$H NMR study of a mixture of DD-ST10 and dA$_{10}$ was attempted. Initially the $^1$H NMR spectra of both components were recorded separately (at a concentration of 0.53 mM for the DD-ST10 and 0.67 mM for the dA$_{10}$ in 10% D$_2$O in H$_2$O), which showed the expected resonances. On addition of 20 mol % of dA$_{10}$ (as a concentrated aqueous solution) to a solution of 0.5 mM of DD-ST10 in 10% D$_2$O—H$_2$O, an immediate precipitation occurred, and it was clear that a structure of the complex in solution could not be determined.

EXPERIMENTAL

Figure 1:
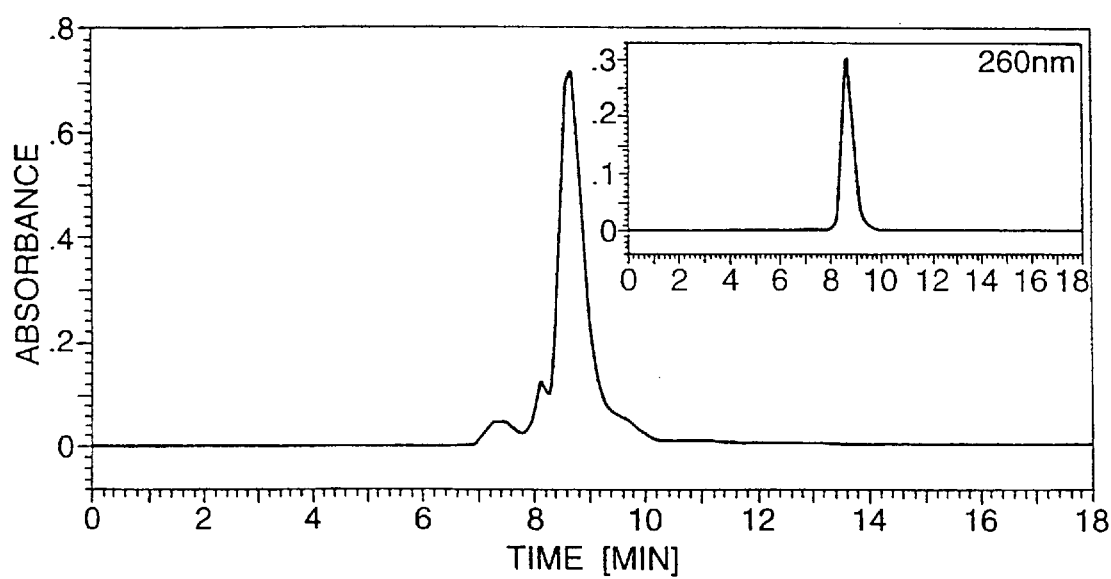
FIG. 1: Reverse phase hplc chromatogram of the crude decamer peptide nucleic acid H-Gly-D-Pro(cis-4-G)-Gly-D-Pro(cis-4T)-Gly-D-Pro(cis-4-A)-Gly-D-Pro(cis-4-G)-Gly-D-Pro(cis-4-A)-Gly-D-Pro(cis-4-T)-Gly-D-Pro(cis-4-C)-Gly-D-Pro(cis-4-A)ly-D-Pro(cis-4-C)-Gly-D-Pro(cis-4-T)-Lys-NH2; Inset: Hplc chromatogram of the purified peptide nucleic acid under identical conditions; Hplc conditions: μBondapak C-18 reverse phase hplc column; solvents: A=0.1% TFA in acetonitrile B=0. 1% aqueous TFA isocratic A:B 10:90; flow rate 1.5 ml/min; detection wavelength 260 nm.
Figure 2:
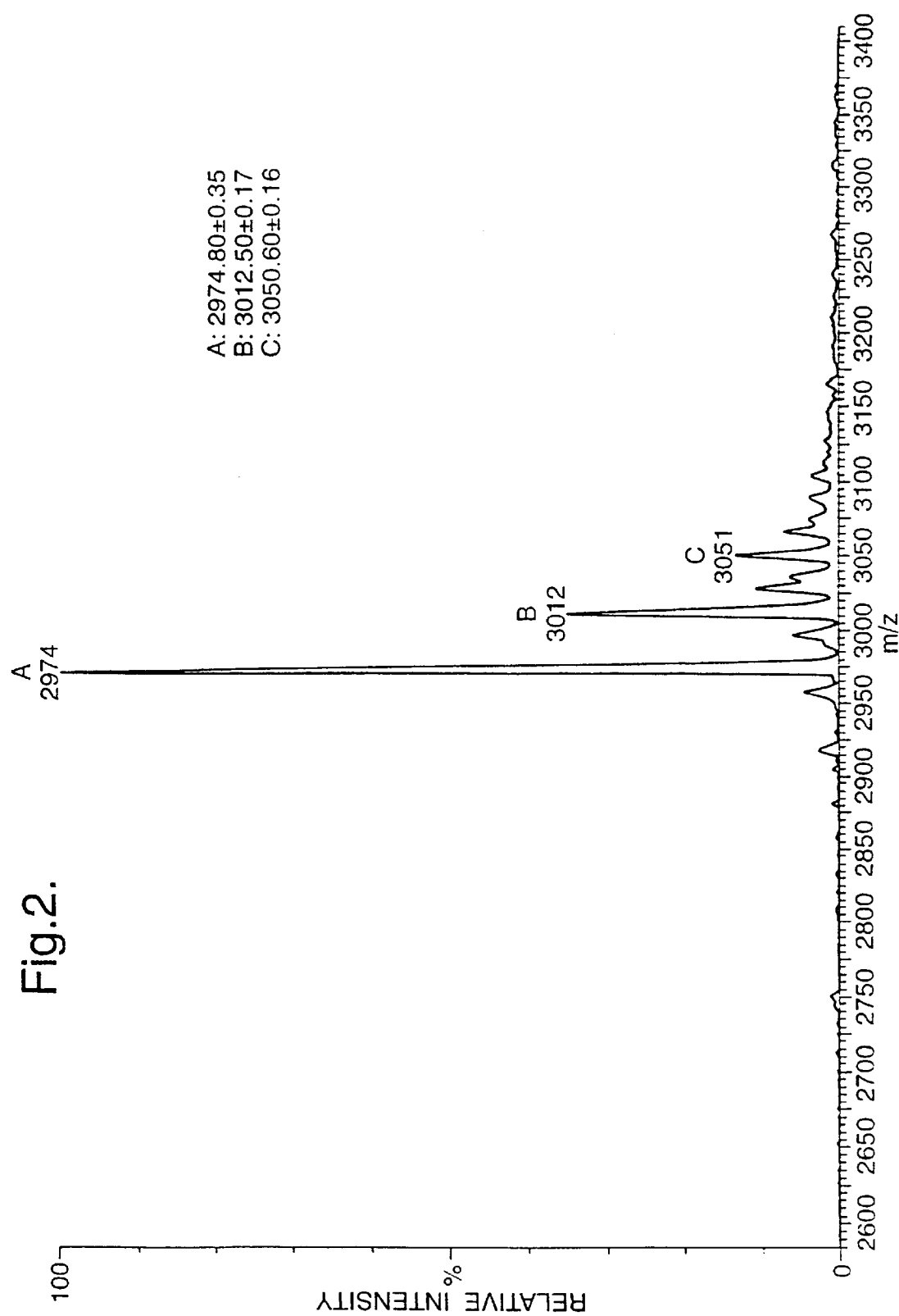
FIG. 2: Electrospray mass spectrum of the purified peptide nucleic acid decamer H-Gly-D-Pro(cis-4-G)-Gly-D-Pro (cis-4-T)-Gly-D-Pro(cis-4-A)-Gly-D-Pro(cis-4-G)-Gly-D-Pro(cis-4-A)-Gly-D-Pro(cis-4-T)-Gly-D-Pron(cis-4-C)-Gly-D-Pro(cis-4-A)-Gly-D-Pro(cis-4-C)-Gly-D-Pro(cis-4-T)Lys-NH$_2$. The potassium adducts [$M_r$=3012 (M+K$^+$–H$^+$) and 3051 (M+2K$^+$–2H$^+$)] were also observed in addition to the product ($M_r$=2974).
Figure 3:
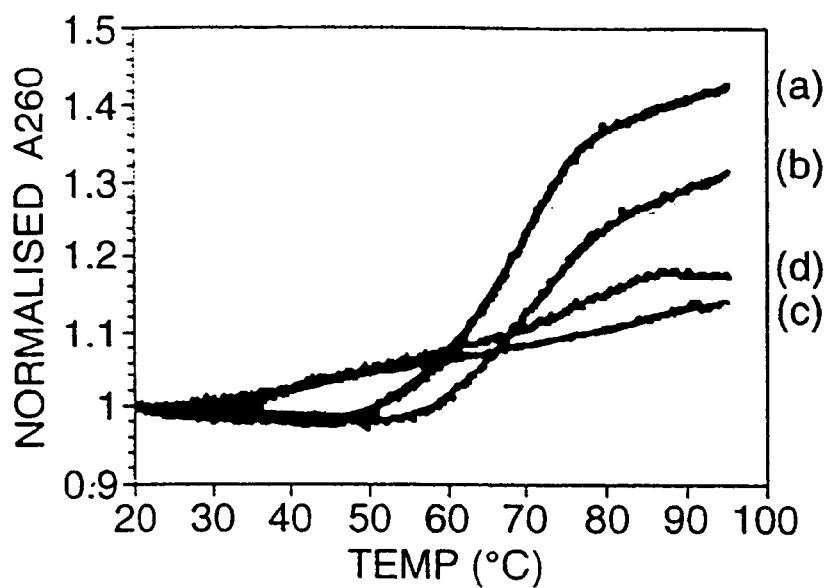
FIG. 3. The melting curves of the 1:1 hybrids of (a) H-[Gly-L-Pro(cis-4-T)]$_{10}$-Lys-NH$_2$, (b) H-[Gly-D-Pro(cis-4-T)]$_{10}$-Lys-NH$_2$, (c) H-[Gly-D-Pro(trans-4-T)]$_{10}$-Lys-NH$_2$ with poly(dA) at 150 mM NaCl, 10 mM sodium phosphate, pH 7.0 and (d) poly(dA) alone. The poly(dA) concentration was 10.8 μM dA nucleotide. The melting curves were recorded at 260 nm and the rate of heating was 0.5° C./min.
Figure 4:
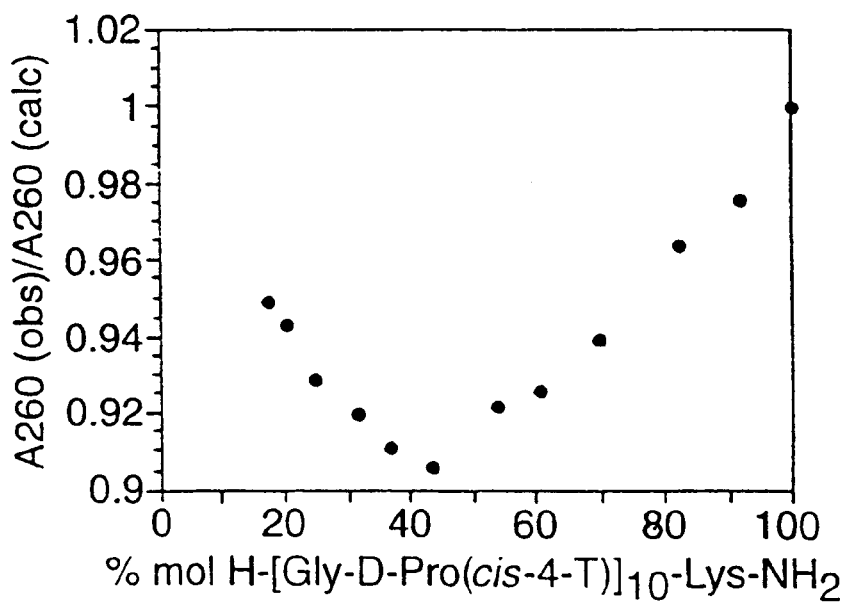
FIG. 4. (Titration of the chiral PNA H-[Gly-D-Pro(cis-4-T)]$_{10}$-Lys-NH$_2$ with poly(rA) at 20° C. Calculated amounts of poly(rA) in 10 mM sodium phosphate buffer pH 7.0 (0.282 mM rA nucleotide) were added to a solution of 16.5 μM H-[Gly-D-Pro(cis-4-T)]$_{10}$-Lys-NH$_2$ in the same buffer. The ratio of observed OD$_{265}$ to calculated OD$_{260}$ is plotted against % mol of H-[Gly-D-Pro(cis-4-T)]$_{10}$-Lys-NH$_2$.

Melting points were recorded on a Kofler block apparatus and are quoted uncorrected. Specific rotations were measured on a Perkin-Elmer 241 polarimeter. IR spectra were recorded on a Perkin-Elmer 1750 Fourier Transform Infrared spectrometer. Elemental analyses were performed on a Carlo Erba CHN analyser model 1106.

Routine $^1$H and $^{13}$C nmr spectra were recorded on a Varian Gemini 200 spectrometer operating at 200 MHz ($^1$H) and 50.28 MHz ($^{13}$C). $^{13}$C spectra were recorded in broad band decoupled mode and the chemical shift assignment was assisted by a DEPT experiment performed on the Varian Gemini 200 spectrometer. High field $^1$H nmr were recorded on a Bruker AMX 500 spectrometer (500 MHz). $^{19}$F nmr spectra were recorded on a Bruker AM 250 at 235.35 MHz $^1$H and $^{13}$C chemical shifts are quoted in ppm relative to tetramethylsilane and were internally referenced to the residual protonated solvent signal. $^{19}$F chemical shifts were extemally referenced to CFCl$_3$ in CHCl$_3$.

Chemical ionisation and fast atom bombardment mass spectra were recorded on a VG 20–0250 masslab and a VG Micromass ZAB-1F mass spectrometer. Electrospray mass spectra were recorded on a VG Biotech BioQ or VG Biotech Platform. Masses are quoted as m/z unless otherwise stated, only the molecular ions and major fragments being quoted.

Distilled water was used for all chemical experiments. Chemicals and solvents were obtained from Aldrich Chemical Company Ltd., Avocado Research Chemicals Ltd. and Lancaster Synthesis Ltd. and were purified according to the literature,[21] if necessary. N-Boc-trans-4-hydroxy-L-proline and Fmoclycine pentafluorophenyl ester were obtained from CalbiochemNovabiochem Ltd. p-Toluenesulfonyl chloride was purified by recrystallisation from petroleum ether (b.p. 60–80° C.). DMF was peptide synthesis grade obtained from Rathbum Chemical Ltd. and was used without further purification except when strictly anhydrous conditions were required where it was redistilled from calcium hydride under reduced pressure. Acetonitrile was hplc grade obtained from Rathbum and used without further purification. THF and dioxane were distilled from sodium wire/benzophenone under argon and stored over 4A molecular sieve. Pyridine was distilled from calcium hydride and stored over 4A molecular sieve. Moisture-sensitive reactions were performed under argon in flame-dried glassware.

N-tert-Butoxycarbonyl-tans-4-hydroxyproline-L-diphenylmethyl ester (2a) and N-tert-butoxycarbonyl-cis-4-hydroxy-D-proline diphenylmethyl ester (2b)

To a solution of freshly prepared diphenyldiazomethane[22] (3.50 g, 18.0 mmol) in ethyl acetate (20 ml) was added N-Boc-trans-4-hydroxy-L-proline (3.25 g. 14.0 mmol) in ethyl acetate (30 ml). Nitrogen gas was slowly evolved from the solution and the intense purple colour of diphenyldiazomethane was gradually discharged. The solution was stirred at room temperature overnight using a CaCl$_2$ guard tube. Evaporation of the solvent followed by precipitation of the product from ethyl acetate-petroleum ether b.p. 40–60° C. gave a white solid, N-tert-butoxycarbonyl-trans-4-hydroxy-L-proline diphenylmethyl ester (2a), (5.10 g, 91%), m.p. 93–95° C. (lit.$^9$ m.p. 103–104° C.), $\delta_H$ (200 MHz; CDCl$_3$) 1.22 and 1.47 (9H, 2xs, Boc rotamers), 1.95–2.50 [3H, br m, CH$_2$(3) and OH], 3.45–3.74 [2H, br m, CH$_2$(5)], 4.40–4.65 [2H, br m, CH(2) and CH(4)], 6.95 (1H, br s, CHPh$_2$), 7.25–7.55 (10H, br m, phenyl CH); $\nu_{max}$ (KBr)/cm$^{-1}$ 3491br (O—H), 1728s (C=O ester), 1693s (C=O urethane); m/z (ES MS) 436 (M+K$^+$, 55%), 420 (M+Na$^+$, 100), 415 (M+NH$_4^+$, 15), 398 (M+H$^+$, 72); $[\alpha]_D^2$ −5−54.3 (c=10, EtOH).

The cis-D-diastereoisomer was prepared similarly starting from N-Boc-cis-hydroxy-D-proline (11.6 g, 50.0 mmol) and diphenyidiazomethane (11.3 g, 58.0 mmol) in ethyl acetate (150 ml). N-tert-Butoxycarbonylcis-4-hydroxy-D-proline diphenylmethyl ester (2b) was obtained as a white solid after precipitation from ethyl acetate-petroleum ether b.p. 40–60° C. (17.9 g, 90%) m.p. 102–105° C., (Found C, 69.5; H, 6.8; N, 3.3%; C$_{23}$H$_{27}$NO$_5$ requires C, 69.5; H, 6.8; N, 3.5%), $\delta_H$ (200 MHz; CDCl$_3$) 1.26 and 1.30 (9H, 2xs, Boc rotamers), 2.08 and 2.35 [2H, m, CH$_2$(3)], 2.88 and 3.09 (1H, 2xd, J=9.6 Hz, OH rotamers), 3.57–3.66 [2H, br m, CH$_2$(5)], 4.32 [2H, m, CH(4)], 4.42–4.58 [1H, m, CH(2)]6.91 and 6.99 (1H, 2xs, CHPh$_2$ rotamers), 7.25–7.48 (10 H, br m, phenyl CH); $\delta_C$ (50.28 MHz; CDCl$_3$) 28.0 and 28.3 (Boc CH$_3$ rotamers), 37.6 and 38.6 [CH$_2$(3) rotamers], 55.4 and 55.9 [CH$_2$(5) rotamers]58.0 and 58.1 [CH(2) rotamers], 70.1 and 71.2 [CH(4) rotamers], 78.1 and 78.6 (CHPh$_2$ rotamers), 80.4 and 80.6 (Boc C), 127.2–128.8 (phenyl CH rotamers), 139.6 and 139.8 (phenyl C rotamers), 154.1 (Boc CO), 174.0 (ester CO rotamers); $\nu_{max}$ (KBr)/cm$^{-1}$ 3466br (O—H), 1749s (C=O ester), 1687s (C=O urethane); $[\alpha]_D^{25}$ +41.2 (c=1.0, EtOH).

N-tert-Butoxycarfonyltrans-4-hydroxy-D-proline diphenylmethyl ester (2c)

N-Boc-cis-hydroxy-D-proline diphenylmethyl ester (2b) (0.20 g, 0.50 mmol), triphenylphosphine (0.160 g, 0.60 mmol) and formic acid (25 μl, 0.65 mmol) were dissolved in dry THF (10 ml) and cooled in an ice bath. DEAD (100 μL, 0.60 mmol) was added dropwise. The reaction mixture was stirred under nitrogen at room temperature overnight. The solvent was evaporated and the residue was chromatographed on silica gel using dichloromethane:acetone 20:1 as eluant to give the 4-formate ester (R$_f$ 0.50) as a colourless oil (0.248 g, quant.), $\delta_H$ (200 MHz; CDCl$_3$) 1.25 and 1.47 (9H, 2xs, Boc rotamers), 2.10–2.55 [2H, br m, CH$_2$(3)], 3.57–3.80 [2H, br m, CH$_2$(5)], 4.48–4.64 [1H, m, CH(2)], 5.3–5.43 [1H, br m, CH(4)], 6.91 and 6.95 (1H, 2xs, CHPh$_2$ rotamers), 7.25–7.42 (10H, br m, phenyl CH), 8.03 [1H, s, HC(O)].

The oil was taken up in methanol (10 ml) and concentrated aqueous ammonia (d0.880; 0.5 ml) was added. Tlc analysis indicated complete reaction after stirring at room temperature for 1 h. The solvent was removed under reduced pressure and the residue chromatographed on silica gel column using diethyl ether as eluant to give the product (R$_f$ 0.30) as a white foam (0.179 g, 90% from 2b), which was further purified by reprecipitation from ethyl acetate-petroleum ether (b.p. 40–60° C.) to give. N-tert-butoxycarbonyl-trans-4-hydroxy-D-profine diphenylmethyl ester (2c) as a white solid, m.p. 105–108° C., (Found C, 69.8; H, 6.9; N, 3.3%; C$_{23}$H$_{27}$NO$_5$ requires C, 69.5; H, 6.8; N, 3.5%), $\delta_H$(200 MHz; CDCl$_3$) 1.22 and 1.47 (9H, 2xs, Boc rotamers), 2.02 and 2.30 [2H, 2x br m, CH$_2$(3)], 2.70 and 2.82 (1H, 2xbr d, J=3.1 and 3.4 Hz, OH rotamers), 3.45–3.70 [2H, br m, CH$_2$(5)], 4.42–4.65 [2H, br m, CH(2)and CH(4)], 6.90 and 6.95 (1H, 2xs, CHPh2), 7.25–7.45 (10H, br m, phenyl CH); $\delta_C$ (50.28 MHz; CDCl$_3$) 27.9 and 28.3 (Boc CH$_3$ rotamers), 38.1 and 38.9 [CH$_2$(3) rotamers], 54.7 [CH$_2$(5)], 57.8 and 58.1 [CH(2) rotamers], 69.2 and 70.0 [CH(4) rotamers], 77.2 and 77.6 (CHPh$_2$ rotamers), 80.6 (Boc C), 127.1–128.8 (phenyl CH rotamers), 140.0 and 140.2 (phenyl C rotamers), 154.4 (Boc CO), 172.0 (ester CO); $\nu_{max}$ (KBr)/cm$^{-1}$ 3491br (O—H), 1728s (C=O ester), 1693s (C=O urethane); $[\alpha]_D^{25}$ +53.0 (c=1.0, EtOH).

N-tert-Butoxycarbonyl-trans-4-(p-toluenesulfonyloxy)-D-proline diphenylmethyl ester (7)

A solution of N-Boc-cis-4-hydroxy-D-proline diphenylmethyl ester 2b) (6.40 g, 16.1 mmol), triphenylphosphine (4.50 g, 16.8 mmol) and methyl-p-toluenesuffonate (3.04 9, 16.4 mmol) in THF was treated with DEAD (2.80 ml, 4.2 mmol) dropwise at −78° C. The reaction was allowed to gradually warm to room temperature and the stirring continued overnight. Evaporation followed by column chromatography (SiO$_2$, diethyl ether, R$_f$ 0.61) gave the crude product as an oil which was re-precipitated from diethyl ether-petroleum ether b.p. 40–60° C. to give the essentially pure product as a white solid (6.01 g, 68%). Recrystallisation from ethyl acetate-petroleum ether (b.p.40–60° C.) gave N-tert-butoxycarbonyl-trans-4-(p-toluenesulfonyloxy)-D-proine diphenylmethyl ester (7) as white crystals, m.p. 147–149° C., (Found C, 65.2; H, 5.8; N, 2.4%; $C_{30}H_{33}NO_7S$ requires C, 65.3; H, 6.0; N, 2.5%), $\delta_H$ (200 MHz; $CDCl_3$) 1.22 and 1.44 (9H, 2xs, Boc rotamers), 1.89–2.18 and 2.32–2.66 [2H, m, $CH_2(3)$], 2.46 (3H, s, tosyl $CH_3$), 3.53–3.74 [2H, m, $CH(5)$], 4.50 [1H, m, $CH(2)$], 4.98 [1H, br m, $CH(4)$], 6.87 and 6.92 (1H, 2xs, $CHPh_2$ rotamers), 7.25–7.38 (12H, m, aromatic $CH$), 7.77 (2H, d, J=8.2 Hz, tosyl $CH$); $\delta_C$ (50.28 MHz; $CDCl_3$) 21.6 (tosyl $CH_3$), 27.9 and 28.2 (Boc CE3 rotamers), 35.6 and 37.0 [$CH_2(3)$ rotamers], 51.8 and 52.1 [$CH_2(5)$ rotamers], 57.4 and 57.6 [$CH(2)$ rotamers], 78.3 and 78.9 [$CH(4)$ rotamers], 78.2 and 78.7 ($CHPh_2$ rotamers), 80.7 and 80.9 (Boc $C$ rotamers), 127.0–130.3 (aromatic $CH$), 133.5, 139.9 and 145.3 (aromatic $C$), 154.6 and 154.8 (Boc $CO$ rotamers), 171.3 (ester $CO$ rotamers); $\nu_{max}$ (KBr)/cm$^{-1}$ 1742s (C=O ester), 1704 (C=O urethane), 1402s (—$SO_2O$—), 1174s (—$SO_2$—).

N-tert-Butoxycarbony-4-($N_3$-benzoyltiymin-1-yl)proline diphenylmethyl esters (3a), (3b) and (3c)

N-Boc-trans-4-hydroxy-Lroline diphenylmethyl ester (2a) (0.425 g, 1.07 mmol), triphenylphosphine (0.290 g, 1.10 mmol) and $N_3$-benzoylthymine (0.250 g, 1.09 mmol) were dissolved in dry THF (10 ml) and the solution was cooled to −15° C. DEAD (180 μL, 1.10 mmol) was then added dropwise with stirring. The reaction mixture was stirred under argon at room temperature overnight. The solvent was evaporated and the residue was chromatographed on silica gel using dichloromethane-acetone 20:1 as eluant to give N-tert-butoxycarbony-cis-4-($N_3$-benzoylthymin-1-yl)-L-proline diphenylmethyl ester (3a) ($R_f$ 0.56), which was recrystallised from ethanol to give a white fluffy solid (0.310 g, 51%), m.p. 183–185° C., (Found C, 68.9; H, 5.5; N, 6.7%; $C_{35}H_{35}N_3O_7$ requires C, 69.0; H, 5.8; N, 6.9%), $\delta_H$ (200 MHz; $CDCl_3$) 1.30 and 1.49 (9H, 2xbr s, Boc rotamers), 1.82 (3H, br s, thymine $CH_3$), 2.05 and 2.85 [2H, br m, $CH_2(3')$], 3.65 (1H, br m) and 4.02 (1H, dd, J=12.0, 8.0 Hz)[$CH_2(5')$], 4.54 [1H, br m, $CH(2')$], 5.26 [1H, br m, $CH(4')$], 6.94 (1H, s, $CHPh_2$), 7.12 and 7.18 [1H, 2xbr s, $CH(6)$ rotamers], 7.30–7.42 (10H, br m, phenyl $CH$), 7.50 (2H, t, J=7.9 Hz, benzoyl m-$CH$), 7.67 (1H, t, J=7.0 Hz, benzoyl p-$CH$), 7.92 (2H, d, J=7.0 Hz, benzoyl o-$CH$); $\delta_C$ (50.28 MHz; $CDCl_3$) 12.3 (thymine $CH_3$), 27.9 and 28.2 (Boc $CH_3$ rotamers), 34.9 and 35.3 [$CH_2(3')$ rotamers], 49.3 and 49.4 [$CH_2(5')$ rotamers], 52.1 and 52.5 [$CH(4')$ rotamers], 57.5 [$CH_2(2')$], 78.1 and 78.4 ($CHPh_2$ rotamers), 81.3 (Boc $C$), 111.7 [$C(5)$], 126.9–130.6 (aromatic $CH$), 131.6 (benzoyl $C$), 135.3 (benzoyl p-$CH$), 136.0 and 136.2 [$CH(6)$ rotamers], 139.4 (phenyl C), 150.1 [$C(2)$], 153.6 (Boc $CO$), 162.6 [$C(4)$], 169.1 (benzoyl $CO$), 171.6 (ester $CO$); m/z (FAB+) 632 (M+Na$^+$, 10%), 610 (M+H$^+$, 39), 554 ([M−$C_4H_8$+H]$^+$, 27), 506 ([M−PhCO+H]$^+$, 18), 338 ([M−PhCO-$Ph_2CH^+$, 20), 266 (31), 231 (BzT+H$^+$, 52), 167 ($Ph_2CH^+$, 100), 105 (PhCO$^+$, 24), 57 ($C_4H_9^+$, 28); $\nu_{max}$ (KBr)/cm$^{-1}$ 1751, 1694 and 1659 (C=O); $[\alpha]_D^{31}$ −17.2 (c=1.0, DMF).

N-tert-Butoxycarbonyl-trans-4($N_3$-benzoylthymin-1-yl)-D-proline diphenylmethyl ester (3b) was similarly prepared starting from the cis-D alcohol (2b) (8.0 g, 20 mmol). The product was obtained as a white solid after column chromatography (SiO$_2$, dichloromethane-acetone 20:1) and trituration with diethyl ether (4.20 g, 33%). Recrystallisation from ethyl acetate-hexane gave an analytically pure sample as white crystals, m.p. 189–192° C., (Found C, 68.9; H, 5.5; N, 6.7%; $C_{35}H_{35}N_3O_7$ requires C, 69.0; H, 5.8; N, 6.9%), $\delta_H$ (200 MHz; $CDCl_3$) 1.30 and 1.47 (9H, 2xs, Boc rotamers), 1.80 (3H, s, thymine $CH_3$), 2.40 and 2.58 (2H, m, $CH_2(3')$], 3.55–4.02 [2H, m, $CH_2(5')$], 4.53–4.64 [1H, m, $CH(2')$], 5.12 [1H, m, $CH(4')$], 6.90 and 6.94 (1H, 2xs, $CHPh_2$ rotamers), 7.00 [1H, s, $CH(6)$ rotamers], 7.35–7.45 (10H, br m, phenyl $CH$), 7.52 (2H, t, J=8.0 Hz, benzoyl m-$CH$), 7.69 (1H, t, J=7.2 Hz, benzoyl p$CH$), 7.94 (2H, J7.2 Hz, benzoyl o-$CH$); $\delta_H$ (50.28 MHz; $CDCl_3$) 12.6 (thymine $CH_3$), 27.9 and 28.2 (Boc $CH_3$ rotamers), 33.4 and 35.1 [$CH_2(3')$ rotamers], 49.1 and 49.5 [$CH_2(5')$ rotamers], 53.8 and 54.4 [$CH(4')$ rotamers], 57.7 and 58.0 [$CH_2(2')$ rotamers], 77.9 and 78.2 ($CHPh_2$ rotamers), 81.2 and 81.3 (Boc $C$ rotamers), 111.9 [$C(5)$], 127.0–130.6 (aromatic $CH$), 131.6 (benzoyl $C$), 135.3 (benzoyl p-$CH$), 136.2 [$CH(6)$], 139.4 and 139.7 (phenyl C rotamers), 149.9 [$C(2)$], 153.6 (Boc CO), 162.7 [$C(4)$], 169.1 (benzoyl $CO$), 171.0 (ester $CO$); $\nu_{max}$ (KBr)/cm$^{-1}$ 1739s (C=O), 1703s (C=O), 1664s (C=O); $[\alpha]_D^{25}$ +11.3 (c=1.03, DMF).

N-tert-Butoxcarbonyl-cis-4-($N_3$-benzoylthymin-1-yl)-D-proline diphenylmethyl ester (3c) was similarly prepared starting from the trans-D alcohol (2c) (7.62 g, 19.2 mmol). The product was obtained as a white crystalline solid after column chromatography (SiO$_2$, dichloromethane-acetone 20:1) and recrystallisation from ethanol (4.20 g, 36%), m.p. 183–186° C., (Found C, 69.1; H, 5.8; N, 6.8% C; $C_{35}H_{35}N_3O_7$ requires C, 69.0; H, 5.8; N, 6.9%), $\delta_H$ (200 MHz; $CDCl_3$) 1.30 and 1.49 (9H, 2xbr s, Boc rotamers), 1.81 (3H, br s, thymine $CH_3$), 2.04 and 2.86 [2H, 2xbr m, C$H_2(3')$], 3.66 (1H, br m) and 4.02 (1H, dd, J=12.0, 8.0 Hz) [$CH_2(5')$, 4.53 [1H, br m, $CH(2')$], 5.26 [1H, br m, $CH(4')$], 6.95 (1H, s, $CHPh_2$), 7.12 and 7.18 [1H, 2xbr s, $CH(6)$ rotamers], 7.30–7.44 (10H, br m, phenyl $CH$), 7.50 (2H, t, J=7.9 Hz, benzoyl m-$CH$), 7.67 (1H, t, J=7.0 Hz, benzoyl p-$CH$), 7.92 (2H, d, J=7.0 Hz, benzoyl o-$CH$); $\nu_{max}$ (KBr) cm$^{-1}$ 1751s (C=O), 1699s (C=O), 1661s (C=O); $[\alpha]_D^{25}$ +16.9 (c=1.03, DMF).

N-tert-butoxycarbonyl-cis-4-($N_6$-benzoyladenin-9yl)-D-proline diphenylmethyl ester (8)

A mixture of the trans tosylate (7) (0.552 g, 1.00 mmol), $N_6$-benzoyladenine (0.595 g, 2.50 mmol), anhydrous $K_2CO_3$ (0.700 g, 5.00 mmol) and 18-crown-6 (0.100 g) in DMF (5 ml) was stirred under argon at 80° C. overnight. The reaction mixture was diluted with dichloromethane (20 ml) and washed with water, dried (MgSO$_4$) and evaporated to give the crude product, which was purified by column chromatography (SiO$_2$, 2.5% methanol in dichloromethane, $R_f$ 0.27) to give the product as a white foam (0.260 g, 42%) which was spectroscopically pure. Further recrystallisation from ethanol-water gave an analytically pure N-tert-butoxycarbonyl-cis-4-($N_6$-benzoyladenin-9-yl)-D-proline diphenylmethyl ester (8) as colourless needles, m.p. 115–119° C., (Found C, 65.9; H, 5.5; N, 13.1%; $C_{35}H_{34}N_6O_5 \cdot H_2O$ requires C, 66.0; H, 5.7; N, 13.2%), $\delta_H$ (200 MHz; $CDCl_3$) 1.31 and 1.49 (9H, 2xs, Boc rotamers), 2.52 and 2.90 [2H, 2xbr m, $CH_2(3')$, 3.90–4.20 [2H, br m, C$H_2(5')$], 4.52 and 4.63 [1H, 2xbr m, $CH(2')$ rotamers], 5.14 [1H, br m, $CH(4')$], 6.83 (1H, s, $CHPh_2$), 7.15–7.28 (10H, m, phenyl $CH$), 7.35–7.60 (m, 3H, benzoyl m- and p-$CH$), 7.95–8.05 [3H, m, $CH(8)$ and benzoyl o-$CH$], 8.68 [1H, s, C$H(2)$], 9.39 (1H, s, N$H$); $\delta_C$ (50.28 MHz; $CDCl_3$) 28.0 and 28.2 (Boc $CH_3$ rotamers), 34.5 and 35.7 [$CH_2(3')$ rotamers], 49.9 and 50.5 [$CH_2(5')$ rotamers], 52.3 and 52.8 [$CH(4')$ rotamers], 57.6 [$CH(2')$], 77.8 ($CHPh_2$), 81.3 (Boc $C$), 123.4 [$C(5)$], 127.0–129.0 (aromatic $CH$), 132.9 (aromatic $CH$), 133.9 (aromatic $C$), 139.4 and 139.5 (aromatic $C$), 141.5 [$CH(8)$], 149.8 [$C(4)$], 152.0 [$C(6)$], 152.7 [$CH(2)$]1,153.6 and 154.0 (Boc $CO$ rotamers), 165.1 (benzoyl $CO$), 170.9 (ester $CO$); m/z (ES MS) 619 (M+H$^+$, 100%); $\nu_{max}$ (KBr)/ cm$^{-1}$ 1748 (C=O), 1697s (C=O); $\nu_{max}$ (CHCl$_3$)/nm 285 ($\epsilon$/dm$^3$·mol$^{-1}$·cm$^{-1}$ 2.1×10$^4$); [$\alpha$]$_D^{25}$ +14.1 (c=0.63, CHCl$_3$).

N-tert-Butoxycarbonyl-cis-4-(N-4-benzoykytosin-1-yl)-D-proline diphenylmethyl ester (11) and N-tert-butoxycarbonyl-cis-4-(4-benzoylaminopyrimidin-2-oxy)-D-proine diphenylmethyl ester A reaction mixture containing the trans-D tosylate (7) (1.10 g, 2.00 mmol), N$_4$-benzoylcytosine (0.475 g, 2.20 mmol), anhydrous K$_2$CO$_3$ (0.300 g, 2.20 mmol) and 18-crown-6 (200 mg) in DMF (10 ml) was stirred at 70–80° C. under argon overnight. The white suspension was diluted with dichloromethane (75 ml), filtered through celite and the organic phase washed with water. Evaporation gave the crude product as an oil which was purfied by column chromatography (SiO$_2$, ethyl acetate). The more polar fractions (R$_f$ 0.33) were combined and evaporated to give the N$_1$-isomer (0.299 g, 25%) as a white foam. Recrystallisation from ethanol-water gave white crystals of N-tert-butoxycarbonyl-cis-4-(N$_4$-benzoylcytosin-1-yl)-D-proline diphenylmethyl ester (11), m.p. 133–135° C., (Found C, 65.8; H, 6.5; N, 8.8%; C$_{34}$H$_{34}$N$_4$O$_6$. C$_2$HR$_5$OH.H$_2$O requires C, 65.6; H, 6.4; N, 8.5%), $\delta_H$ (200 MHz; CDCl$_3$) 1.30 and 149 (9H, 2xs, Boc rotamers), 2.20 and 2.90 [2H, br m, CH$_2$(3')], 3.50–3.80 and 3.95–4.15 [2H, 2xbr m, CH$_2$(5')], 445–4.70 [1H, br m, CH(2')], 5.28 [1H, br m, CH(4')], 6.87 (1H, s, CHPh$_2$), 7.15–7.40 (10H, m, phenyl CH), 7.40–7.75 [5H, m, CH(5), CH(6) and benzoyl m- and p-CH], 7.89 (2H, d, J=7.4 Hz, benzoyl o-CH), 8.83 (1H, br s, NH); $\delta_C$ (50.28 MHz; CDCl$_3$) 27.7 and 28.0 (Boc CH$_3$ rotamers), 34.4 and 36.0 [CH$_2$(3') rotamers], 49.6 and 50.5 [CH$_2$(5') rotamers], 54.3 and 54.9 [CH(4') rotamers], 57.6 CH(2')], 78.0 and 78.3 (CHPh$_2$ rotamers), 81.3 (Boc C), 96.8 [CH(5)], 127.0–129.2 (aromatic CH), 133.4 (benzoyl C), 139.5 (aromatic C), 145.2 and 145.7 [CH(6) rotamers)], 153.8 (Boc CO rotamers), 155.6 [C(2)], 162.0 [C(4)], 166.8 (benzoyl CO), 171.3 (ester CO); m/z (ES MS) 595 (M+H$^+$, 100%); $\nu_{max}$ (KBr)/cm$^{-1}$ 1743 (C=O), 1704s (C=O); $\lambda_{max}$ (CHCl$_3$)/nm 266 ($\epsilon$/dm$^3$.mol$^{-1}$.cm$^{-1}$ 8.9×10$^4$), 312 (3.4×10$^4$); [$\alpha$]$_D^{25}$ −13.6 (c=0.50, CHCl$_3$).

The less polar fractions (R$_f$ 0.61) were combined and re-chromatographed (SiO$_2$, dichforomethane:acetone 10:1) to give the O$_2$-isomer as a white foam (0.489 g, 41%) which was recrystallised from ethanol to give colourless needles of N-tert-butoxycarbonyl-cis-4-A(4-benzoylaminopynmidin-2-oxy)-D-prorine diphenylmethyl ester m.p. 145–147° C., (Found C, 68.6; H, 5.5; N, 9.4%; C$_{34}$H$_{34}$N$_4$O$_6$ requires C, 68.7; H, 5.8; N, 9.4%). $\delta_H$ (200 MHz; CDCl$_3$) 1.27 and 1.46 (9H, 2xs, Boc rotamers), 2.42 and 2.63 [2H, br m, CH$_2$(3')], 3.60–4.20 [2H, br m, CH$_2$(5')], 4.50 and 4.70 [1H, 2xm, CH(2')], 5.40 [1H, br m, CH(4')], 6.91 and 6.98 (1H, s, C HPh$_2$), 7.15–7.32 (10H, m, phenyl CH), 7.46–7.62 (3H, m, benzoyl m- and p-CH), 7.70–7.94 13H, m, benzoyl o-CH and CH(5)], 8.37 [1H, d, J=5.7 Hz, CH(6)], 8.67 (1H, br s, NH); $\delta_C$ (50.28 MHz; CDCl$_3$) 27.9 and 28.3 (Boc CH$_3$ rotamers), 35.1 and 36.0 [CH$_2$(3') rotamers], 51.7 and 52.1 [CH$_2$(5') rotamers], 57.6 and 57.9 [CH(2') rotamers], 74.1 and 75.2 [CH(4') rotamers], 77.3 and 77.5 (CHPh$_2$ rotamers), 80.2 and 80.4 (Boc C rotamers), 104.7 [CH(5)], 127.1–129.2 (aromatic CH), 133.1 and 33.4 (benzoyl C), 140.0–140.3 (aromatic C), 154.0 and 154.4 (Boc CO rotamers), 159.6 [C(2)], 160.5 [CH(6) rotamers], 163.8 [C(4)], 166.3 (benzoyl CO), 170.9 and 171.1 (ester CO); m/z (ES MS) 595 (M+H$^+$, 100 %); $\nu_{max}$ (KBr)/cm$^{-1}$1738s (C=O), 1687s (C=O).

N-tert-Butoxycarbonyl-cis-4-(N$_2$-isobutyrguanin-9-yl)-D-proline diphenylmethyl ester (14)

To a stirred suspension of the transo alcohol (2c) (0.400 g, 1.00 mmol), N$_2$-isobutyryl-O$_6$-nitrophenylethylguanine (0.360 g, 1.00 mmol) and triphenylphosphine (0.294 g. 1.10 mmol) in anhydrous dioxane (10 ml) at room temperature was slowly added DEAD (182 $\mu$L, 1.10 mmol) under argon. Another two aliquots of DEAD (91 ml, 0.55 mmol each) were added during a period of 36 h. The resulting clear yellow solution was evaporated and the residue chromatographed (SiO$_2$, ethyl acetate, R$_f$ 0.46) to give the O$_6$-nitrophenylethyl derivative as a white foam (0.634 g, contaminated with diethyl hydrazinedicarboxylate). This was dissolved in dry pyridine (5 ml containing DBU (300 $\mu$L, 2.00 mmol) and the solution stirred at room temperature overnight under argon. The reaction mixture was diluted with dichloromethane and washed with 5% HCl and water and then evaporated to dryness. The residue was purified by column is chromatography (SiO$_2$, ethyl acetate-methanol 20:1) to give the product as a white foam (0.258 g, 43% from 2c). Recrystallisation from ethyl acetate-petroleum ether (b.p. 40–60° C.) gave N-tert-butoxycarbonylcis-4-(N$_2$-isobutyyylguanin-9-yl)-D-proine diphenylmethyl ester (14) as a white crystalline solid m.p. 140–145° C., (Found C, 64.0; H, 5.7; N, 13.6%; C$_{32}$H$_{36}$N$_6$O$_6$ requires C, 64.0; H, 6.0; N, 14.0%), $\delta_H$ (200 MHz; CDCl$_3$) 1.18–1.41 [15H, m, Boc and (CH$_3$)$_2$CH], 2.30 (1H, br m) and 2.75–2.95 (2H, br m) [C H$_2$(3') and (CH$_3$)$_2$CH], 3.78 and 4.05 [2H, br m, CH$_2$(5')], 4.45–4.63 [1H, 2xm, CH(2')], 4.90 [1H, br m, CH(4')], 6.77 and 6.80 (1H, s, CHPh$_2$), 7.15–7.30 (10H, m, phenyl CH), 7.60 and 7.66 [1H, 2xs, CH(8)]; $\delta_C$ (50.28 MHz; CDCl$_3$) 18.9 [(CH$_3$)$_2$CH], 27.9 and 28.2 (Boc CH$_3$ rotamers), 35.8 [CH$_2$(3')], 50.2 and 50.7 [CH$_2$(5') rotamers], 51.9 and 52.3 CH(4') rotamers], 57.6 [CH(2')], 60.4 [(CH$_3$)$_2$CH], 77.7 and 77.9 (CHPh$_2$ rotamers), 81.1 (Boc C) 121.1 [C(5)], 127.0–128.7 (aromatic CH), 137.2 [CH(8)], 139.5 (aromatic C), 148.2 and 149.1 [C(2)/C(6)], 153.6 and 154.2 (Boc CO rotamers), 156.1 [C(4)], 171.0 (ester CO), 180.5 (amide CO); m/z (ES MS) 601 (M+H$^+$, 100%); $\lambda_{max}$ (CHCl$_3$)/nm 255sh ($\epsilon$/dm$^3$.mol$^{-1}$ 1.5×10$^4$), 282 (1.2×10$^4$); [$\alpha$]$_D^{23}$ +37.8 (c=0.545, CHCl$_3$).

Procedure for Selective Deprotection of N-Boc group in Diphenylmethyl Esters (3a, 3b and 3c) and Synthesis of N-Fmoc Dipeptide Diphenylmethyl Esters (4a, 4b and 4c)

The Boc-protected monomer (3a, 3b, 3c) was dissolved in THF (ca. 10 ml/mmol), saturated methanolic HCl (ca. 10 ml/mmol) was added and the solution was stirred at room temperature for 3–12 h. The solvents were removed under reduced pressure. The residue was taken up in dry dioxane and DIEA (ca. 2 eq excess) was added until the solution was slightly basic (pH 8) when applied to a piece of moist pH paper. Fmoc-glycine pentafluorophenyl ester (1 eq. excess) was then added and the solution stirred at room temperature overnight. The reaction mixture was evaporated to dryness and the residue purified by column chromatography (SiO$_2$, dichloromethane:acetone 10:1).

N-(N-Fluoren-9-ylmethoxycarbonylglycyl)-cis-4-(N3-benzoylthymin-1-yl)-L-proline diphenylmethyl ester (4a) was obtained as a white solid (99%, starting from 5.8 mmol of 3a) after column chromatography. Recrystallisation from ethanol gave fine colourless needles, m.p. 201–204° C., (Found C, 71.5; H, 5.0; N, 7.0%; C$_{47}$H$_{40}$N$_4$O$_8$ requires C, 71.6; H, 5.1; N, 7.0%), $\delta_H$ (200 MHz; CDCl$_3$) 1.72 and 1.85 (3H, 2xs, thymine CH$_3$ rotamers), 2.10, 2.45, 2.72 and 2.95 [2H, 4xm, CH$_2$(3') rotamers], 3.60–3.82 and 3.95–4.09 [4H, br m, CH$_2$(5') and Gly CH$_2$], 4.25 (1H, t, J=7.1 Hz, Fmoc aliphatic CH), 4.40 (2H, d, J=7.1 Hz, Fmoc CH$_2$), 4.77 [1H, br m, CH(2') rotamers], 5.15 and 5.35 [1H, 2xm, CH(4') rotamers], 5.60 and 5.78 [1H, 2xbr m, Glycine NH rotamers], 6.86 and 6.93 (1H, 2xs, CHPh$_2$ rotamers), 6.96 and 7.11 [1H, 2xs, CH(6) rotamers], 7.25–7.95 (m, phenyl, Fmoc and benzoyl aromatic C$\underline{H}$); δ$_C$ (50.28 MHz; CDCl$_3$) 12.1 (thymine C$\underline{H}_3$), 32.5 [C$\underline{H}_2$(3') rotamers], 43.5 (Gly C$\underline{H}_2$), 47.0 (Fmoc aliphatic C$\underline{H}$), 48.5 [C$\underline{H}_2$(5')], 53.2 [C$\underline{H}$(4')], 57.8 [C$\underline{H}_2$(2')], 67.3 (Fmoc C$\underline{H}_2$), 78.7 (C$\underline{H}$Ph$_2$), 112.3 [C(5)], 120.1 (Fmoc aromatic C$\underline{H}$), 125.5–131.8 (aromatic C$\underline{H}$), 135.8 [C$\underline{H}$(6)], 139.4 and 139.6 (phenyl C rotamers), 141.7 and 144.0 (Fmoc aromatic C), 150.0 [C(2)], 156.2 (Fmoc C$\underline{O}$), 162.4 [C(4)], 167.8 (benzoyl C$\underline{O}$), 168.9 (peptide C$\underline{O}$), 170.8 (ester C$\underline{O}$); m/z (FAB+) 811 (M+Na$^+$, 21%), 789 (M+H$^+$, 5),179 {[(C$_6$H$_4$)$_2$C=CH$_2$+H]$^+$, 23}, 167 (Ph$_2$CH$^+$, 100), 105 (PhCO$^+$, 22); ν$_{max}$ (KBr)/cm$^{-1}$ 1751s, 1737s, 1697 and 1657s (C=O); λ$_{max}$ (CHCl$_3$)/nm 260 (ε/dm$^3$.mol$^{-1}$.cm$^{-1}$, 3.1×10$^4$); [α]$_D^{22}$ −41.2 (c=0.50, CHCl$_3$).

N-(N-Fluoren-9-ylmethoxycarbonylglycyl)-trans-4-(N$_3$-benzoylthymin-1-yl)-D-proline diphenylmethyl ester (4b) was obtained as a white solid (85%, starting from 5.3 mmol of 3b) after column chromatography. Recrystallisation from ethanol-water gave a white solid, m.p. 125–128° C., (Found C, 71.4; H, 5.0; N, 6.6%; C$_{47}$H$_{40}$N$_4$O$_8$ requires C, 71.6; H, 5.1; N, 7.1%), δ$_H$ (200 MHz; CDCl$_3$) 1.88 and 1.94 (3H, 2s, thymine C$\underline{H}_3$ rotamers), 2.30 and 2.60 [2H, br m, C$\underline{H}_2$(3') rotamers], 3.70–4.10 [4H, br m, C$\underline{H}_2$(5') and Gly C$\underline{H}_2$], 4.22 (1H, t, J=7.1 Hz, Fmoc aliphatic C$\underline{H}$), 4.39 (2H, d, 7.0 Hz, Fmoc C$\underline{H}_2$), 4.88 [1H, br m, C$\underline{H}$(2')], 5.13 [1H, br m, C$\underline{H}$(4')], 5.90 and 5.98 (1H, 2xbr m, Gly N$\underline{H}$), 6.91 and 6.94 (1H, 2xs, C$\underline{H}$Ph$_2$ rotamers), 7.16 [1H, s, C$\underline{H}$(6)], 7.29–8.00 (m, phenyl, benzoyl and Fmoc aromatic C$\underline{H}$); δ$_C$ (50.28 MHz; CDCl$_3$) 12.4 (thymine C$\underline{H}_3$), 32.0 [C$\underline{H}_2$(3') rotamers], 43.2 and 43.4 (Gly C$\underline{H}_2$ rotamers), 47.0 (Fmoc aliphatic C$\underline{H}$), 48.3 [C$\underline{H}_2$(5')], 55.2 and 55.3 [C$\underline{H}$(4') rotamers], 57.9 [C$\underline{H}_2$(2')], 67.3 (Fmoc C$\underline{H}_2$), 78.6 and 79.3 (C$\underline{H}$Ph$_2$ rotamers), 112.0[C(5)], 120.2 (Fmoc aromatic C$\underline{H}$), 125.4–131.6 (aromatic C$\underline{H}$), 135.6 [C$\underline{H}$(6)], 137.2 and 139.2 (phenyl C rotamers), 141.5 and 144.1 (Fmoc aromatic C), 150.0 [C(2)], 156.9 (Fmoc C$\underline{O}$), 162.9 [C(4)], 168.4 (benzoyl C$\underline{O}$), 169.4 (peptide C$\underline{O}$), 170.1 and 170.5 (ester C$\underline{O}$); m/z (ES MS) 806 (M+NH$_4^+$, 28%), 789 (M+H$^+$, 100); ν$_{max}$ (KBr)/cm$^{-1}$ 1749, 1702 and 1660 (C=O).

N-(N-fluoren-9-ylmethoxycarbonylglycyl)-cis-4-(N$_3$-benzoylthymin-1-yl)-D-proline diphenylmethyl ester (4c) was obtained as a white solid (98%, starting from 5.7 mmol of 3c) after column chromatography (R$_f$ 0.30). Recrystallisation from ethanol-water gave colourless needles m.p. 201–203° C. (Found C, 72.4; H, 4.9; N, 7.2%; C$_{47}$H$_{40}$N$_4$O$_8$ requires C, 71.6; H, 5.1; N, 7.1%), δ$_H$ (200 MHz; CDCl$_3$) 1.71 and 1.83 (3H, 2xs, thymine C$\underline{H}_3$ rotamers), 2.06, 2.42, 2.78 and 2.92 [2H, m, C$\underline{H}_2$(3') rotamers], 3.60–3.82 and 3.90–4.10 ]4H, br m, C$\underline{H}_2$(5') and Gly C$\underline{H}_2$], 4.23 (1H, t, J=7.0 Hz, Fmoc aiiphatic C$\underline{H}$), 4.39 (2H, d, J=7.1 Hz, Fmoc C$\underline{H}_2$), 4.73 [1H, br m, C$\underline{H}$(2') rotamers], 5.14 and 5.42 [1H, 2xm, C$\underline{H}$(4') rotamers], 5.60 and 5.68 [1H, 2xbr m, Gly N$\underline{H}$ rotamers], 6.87 and 6.91 (1H, 2xs, C$\underline{H}$Ph$_2$ rotamers), 6.96 and 7.09 [1H, 2xs, C$\underline{H}$(6) rotamers], 7.21–7.92 (m, phenyl, Fmoc and benzoyl aromatic C$\underline{H}$); m/z (ES MS) 806 (M+NH$_4^+$, 98%), 789 (M+H$^+$, 100); ν$_{max}$ (KBr)/cm$^{-1}$ 1751, 1737, 1697 and 1657 (C=O); λ$_{max}$ (CHCl$_3$)/nm 260 (ε/dm$^3$.mol$^{-1}$.cm$^{-1}$ 3.4×10$^4$); [α]$_D^{22}$ +41.5 (c=0.50, CHCl$_3$).

Procedure Forselective Deprotecton of N-Boc group in Diphenylmethyl Esters (8, 11 and 14) and Synthesis of N-Fmoc Dipeptide Diphenylmethyl Esters (9, 12 and 15)

The Boc-protected monomer (8, 11, 14) and p-toluenesulfonic acid monohydrate (5 eq.) was dissolved in acetonitrile (ca. 5 ml/mmol) and the resulting solution was stirred at room temperature overnight. The solvent was removed under reduced pressure and the residue was dissolved in DMF (ca. 5–10 ml/mmol). DIEA (5 eq. excess) was added until the solution was slightly basic (pH~8) when applied to a piece of moist pH paper followed by HOBt.H$_2$O (1.2 eq.) and Fmoc-glycine pentafluorophenyl ester (1.2 eq.) and the reaction mixture stirred at room temperature overnight. The reaction mixture was diluted with dichloromethane and washed with saturated aqueous NaHCO$_3$ and water. Evaporation gave the crude product which was purified by column chromatography.

N-(N-Fluoren-9-ylmethoxycarbonylglycyl)-cis-4-(N$_6$-benzoyladenin-9-yl)-D-proline diphenylmethyl ester (9) was obtained as a white foam (85%, starting from 1.28 mmol of 8) after column chromatography (SiO$_2$, 10% methanol in ethyl acetate), m.p. 130–133° C., (Found C, 71.0; H, 4.8; N, 12.2%; C$_{47}$H$_{39}$N$_7$O$_6$ requires C, 70.8; H, 4.9; N, 12.3%), δ$_H$ (200 MHz; CDCl$_3$) 2.58 and 2.83 [2H, 2xm, C$\underline{H}_2$(3')], 3.78–4.40 [m, unresolved C$\underline{H}_2$(5'), Gly C$\underline{H}_2$, Fmoc aliphatic C$\underline{H}$ and C$\underline{H}_2$], 4.78 [1H, m, C$\underline{H}$(2')], 5.05 and 5.28 [(1H, 2xm, C$\underline{H}$(4') rotamers], 6.13 (1H, br t, Gly N$\underline{H}$), 6.76 (1H, 2xs, C$\underline{H}$Ph$_2$ rotamers), 7.20–7.75 (m, benzoyl m- and p-C$\underline{H}$, phenyl and Fmoc aromatic C$\underline{H}$), 7.96–8.00 (2H, d, J=7.1 Hz, benzoyl o-C$\underline{H}$), 8.23 [1H, s, C$\underline{H}$(8)], 8.70 [1H, s, C$\underline{H}$(2)], 9.48 (1H, br s, benzamide N$\underline{H}$); δ$_C$ (50.28 MHz; CDCl$_3$) 33.5 [C$\underline{H}_2$(3')], 43.3 (Gly C$\underline{H}_2$), 47.0 (Fmoc aliphatic C$\underline{H}$), 49.4 [C$\underline{H}_2$(5')], 53.2[C$\underline{H}$(4')], 57.8 [C$\underline{H}$(2')], 67.1 (Fmoc C$\underline{H}_2$), 78.6 C$\underline{H}$Ph$_2$), 120.1 (Fmoc aromatic C$\underline{H}$), 123.5 [C(5)], 125.2–128.9 and 133.0 (aromatic C$\underline{H}$), 133.8, 139.4 and 141.4 (aromatic C), 142.0 [C$\underline{H}$(8)], 144.1 (aromatic C), 150.0 [C(4)], 152.1 [C(6)], 152.7 [C$\underline{H}$(2)], 156.9 (Fmoc C$\underline{O}$), 165.4 (benzoyl C$\underline{O}$), 168.6 (Gly C$\underline{O}$), 170.4 (ester C$\underline{O}$); m/z (ES MS) 798 (M+H$^+$, 100%); ν$_{max}$ (KBr)/cm$^{-1}$ 1718 (C=O), 1668 (C=O); [α]$_D^{22}$ +18.6 (c=0.21, CHCl$_3$).

N-(N-Fluoren-9ylmethoxycarbonylglycyl)-cis-4-(N$_4$-benzoylcytosin-1-yl)-D-proline diphenylmethyl ester (12) was obtained as a white foam (70%, starting from 1.12 mmol of 11) after column chromatography (SiO$_2$, ethyl acetate-methanol 20:1). Recrystallisation from ethanol gave a white solid, mp. 131–133° C., (Found C, 71.2; H, 4.9; N, 9.0%; C$_{46}$H$_{39}$N$_5$O$_7$ requires C, 71.4; H, 5.1; N, 9.0%), δ$_H$ (200 MHz; CDCl$_3$) 2.20 and 2.85 [2H, 2xm, C$\underline{H}_2$(3')], 3.61–4.40 [m, unresolved C$\underline{H}_2$(5'), Gly C$\underline{H}_2$, Fmoc aliphatic C$\underline{H}$ and C H$_2$], 4.76–4.81 [1H, m, C$\underline{H}$(2') rotamers], 5.22 and 5.41 [1H, 2xm, C$\underline{H}$(4') rotamers], 6.03 and 6.12 (1H, 2xbr t, Gly N$\underline{H}$ rotamers), 6.78 (1H, br s, C$\underline{H}$Ph$_2$), 7.05–8.00 [m, C$\underline{H}$(5), C$\underline{H}$(6), benzoyl, phenyl and Fmoc aromatic C$\underline{H}$], 9.32 (1H, br s, benzamide N$\underline{H}$); δ$_C$ (50.28 MHz; CDCl$_3$) 33.2 [C$\underline{H}_2$(3')], 43.5 (Gly C$\underline{H}_2$), 47.0 (Fmoc aliphatic C$\underline{H}$), 49.2 [C$\underline{H}_2$(5')], 55.5 [C$\underline{H}$(4')], 57.8 [C$\underline{H}$(2')],67.1 (Fmoc C$\underline{H}_2$), 78.6 (C$\underline{H}$Ph$_2$), 97.3 [C$\underline{H}$(5)], 120.1 (Fmoc aromatic C$\underline{H}$), 125.4–129.1 and 133.1 (aromatic C$\underline{H}$), 133.3, 139.4 and 141.1 (aromatic C), 144.1 (aromatic C), 145.6 [C$\underline{H}$(6)], 155.8 [C(2)], 156.7 (Fmoc C$\underline{O}$), 162.6 and 163.0 [C(4) rotamers], 167.1 (benzoyl C$\underline{O}$), 168.6 (Gly C$\underline{O}$), 170.6 (ester C$\underline{O}$); m/z (ES MS) 774 (M+H$^+$, 100%); ν$_{max}$ (KBr)/cm$^{-1}$ 1750–1665br (C=O); [α]$_D^{22}$ +20.9 (c=0.21, CHCl$_3$).

N-(N-Fluoren-9-ylmethoxycarbonylglycyl)-cis-4-(N$_2$-isobutytylguanin-9-yl)-D-proline diphenylmethyl ester(i5) was obtained as a white solid (52%, starting from 0.73 mmol of 14) after column chromatography (SiO$_{2,10}$% methanol in ethyl acetate). Recrystallisation from ethyl acetate-petroleum ether (b.p. 40–60° C.) gave a white crystalline solid, m.p. 145–150° C., (Found C, 68.0; H, 5.2; N, 12.0%; C$_{44}$H$_{41}$N$_7$O$_7$ requires C, 67.8; H, 5.3; N, 12.6%), δ$_H$ (200 MHz; CDCl$_3$) 1.18 and 1.21 [6H, d, J=6.7 Hz, (C$\underline{H}_3$)$_2$CH], 2.31 (1H, br m) and 2.61–2.79 (2H, br m) [C$\underline{H}$(3') and (CH$_3$)$_2$C$\underline{H}$], 3.89–4.20 [m, unresolved C$\underline{H}_2$(5'), Gly C$\underline{H}_2$ and Fmoc aliphatic C$\underline{H}$], 4.37 (2H, d, J=6.7 Hz, Fmoc C$\underline{H}_2$), 4.63 [1H, m, C$\underline{H}$(2')], 4.82 [1H, m, C$\underline{H}$(4')], 6.10 (1H, br m, Gly N$\underline{H}$), 6.77 (1H, s, C$\underline{H}$Ph$_2$), 7.12–7.36 (m, phenyl and Fmoc aromatic C$\underline{H}$), 7.49–7.57 [3H, m, Fmoc aromatic C$\underline{H}$ and C$\underline{H}$(8)], 7.69–7.73 (2H, d, J=7.4 Hz, Fmoc aromatic C$\underline{H}$), 9.83 (1H, br s, isobutyramide N$\underline{H}$); $\delta_C$(50.28 MHz; CDCl$_3$) 18.9 [C$\underline{H}_3$)$_2$C$\underline{H}$], 35.7 [C$\underline{H}_2$(3')], 42.9 (Gly C$\underline{H}_2$), 46.5 (Fmoc C$\underline{H}$), 49.0 [C$\underline{H}_2$(5')], 52.9 [C$\underline{H}$(4')], 57.7 [C$\underline{H}$(2')], 66.9 (Fmoc C$\underline{H}_2$), 78.3 (C$\underline{H}$Ph$_2$), 120.1 (Fmoc aromatic C$\underline{H}$), 120.9 [C(5)], 125.2–128.8 (Fmoc aromatic C$\underline{H}$), 137.5 [C$\underline{H}$(8)], 139.4 and 139.6 (aromatic C), 144.0 (aromatic C), 148.3 and 148.8 [C(2)/C(6)], 155.8 [C(4)], 157.2 (Fmoc CO), 169.0 (Gly CO), 170.2 (ester CO), 180.6 (isobutyramide CO); m/z (ES MS) 780 (M+H$^+$, 100%); $\lambda_{max}$ (CHCl$_3$)/nm 270sh ($\epsilon$/dm$^3$.mol$^3$.cm$^{-1}$, 11.9×10$^4$); $[\alpha]_D^{23}$ +36.7 (c=0.645, CHCl$_3$).

N-(N-Fluoren-9-ymethoxycarbonylglycyl)-4-(thymin-1-yoprolines (5a), (5b) and (5c)

The protected dipeptide (4a, 4b or 4c) was treated with 10% HBr in acetic acid (5–10 ml/mmol) at room temperature for 1 h. The volatiles were evaporated under reduced pressure, the residue was triturated with diethyl ether and then washed with methanokdiethyl ether.

N-(N-Fluoren-9-ylmethoxycarbonylglycyl)-cis-4-(thymin-1-yl)-L-proline (5a) was obtained as a white solid (50%, starting from 2.5 mmol of 4a). Recrystallisation from ethanol-water gave a white solid, m.p.>200° C., (Found C, 62.5; H, 5.1; N, 10.6%; C$_{27}$H$_{26}$N$_4$O$_7$ requires C, 62.5; H, 5.1; N, 10.8%) $\delta_H$ (200 MHz; DMSO-d$_6$) 1.75 (3H, br s, thymine C$\underline{H}_3$), 2.00–2.35 [2H, br m, C$\underline{H}_2$(3') rotamers], 3.30–4.00 [br m, C$\underline{H}$(5') and Gly C$\underline{H}_2$ obscured by the water signal], 4.15–4.30 (3H, br m, Fmoc aliphatic C$\underline{H}$ and C$\underline{H}_2$), 4.50–4.65 [1H, br m, C$\underline{H}$(2) rotamers], 4.80–4.85 and 4.95–5.05 [1H, br m, C$\underline{H}$(4') rotamers], 7.25–7.45 (4H, m, Fmoc aromatic C$\underline{H}$), 7.52 [1H, br s, C$\underline{H}$(6) rotamers], 7.70 and 7.85 (4H, 2xd, J=7.1 Hz, Fmoc aromatic C$\underline{H}$); m/z (FAB) 541 (M+Na$^+$, 9%), 179 {[C$\underline{H}$(C$_6$H$_4$)$_2$C=CH$_2$.H]$^+$, 81}, 165 (32), 119 (30), 103 (44), 85 (83), 77(32), 59 (85),47(100); $\nu_{max}$ (KBr)/cm$^{-1}$ 1731 (C=O), 1703s (C=O), 1678 (C=O); $[\alpha]_D^{23}$ −213–4.13 (c=0.63, DMF).

N-(N-Fluore-9-ylmethoxrbonylglycyl)-4-thymin-1-yl)-D-proline (5b) was obtained as a white solid (57%, starting from 5.3 mmol of 4b) m.p.>200° C., $\delta_H$ (200 MHz; DMSO$_6$) 1.70 (3H, br s, thymine C$\underline{H}_3$), 2.05–2.15 and 2.40–2.60 [br m, C$\underline{H}_2$(3') rotamers, obscured by the DMSO signal], 3.50–4.00 [br m, C$\underline{H}_2$(5') and Gly C$\underline{H}_2$], 4.15–4.30 (3H, br m, Fmoc aliphatic C$\underline{H}$ and C$\underline{H}$), 4.35–4.45 and 4.75–4.85 [1H, br m, C$\underline{H}$(2') rotamers], 4.90–5.00 and 5.05–5.10 [1H, m, C$\underline{H}$(4') rotamers], 7.25–7.45 (4H, m, Fmoc aromatic C$\underline{H}$), 7.55 [1H, br s, C$\underline{H}$(6)], 7.68 (4H, 2xd, J=7.1 Hz, Fmoc aromatic C$\underline{H}$); m/z (FAB) 519 (M+H$^+$, 6%), 179 {[(C$_6$H$_4$)$_2$C=CH$_2$.H]$^+$, 34}, 85 (100), 59 (23), 47 (32).

N-(N-Fluoren-9-ylmethoxycarbonylglycyl)-cis-4-(thymin-1-yl)-D-proline (5c) was obtained as a white solid (42%, starting from 6.8 mmol of 4c), m.p.>200 C, $\delta_H$ (200 MHz; DMSO-d$_6$) 1.75 (3H, br s, thymine C$\underline{H}_3$), 2.11 and 2.52 [2H, 2xbr m, C$\underline{H}_2$(3') rotamers, 3.50–4.00 [br m, C$\underline{H}_2$(5') and Gly C$\underline{H}_2$], 4.18–4.30 [4H, br m, C$\underline{H}$(2') and Fmoc aliphatic C$\underline{H}$ and C$\underline{H}_2$]4.73 and 4.98 [1H, 2xbr m, C$\underline{H}$(4') rotamers], 7.28–7.41 (4H, m, Fmoc aromatic C$\underline{H}$), 7.51 (1H, m, Gly N$\underline{H}$), 7.54 [1H, br s, C$\underline{H}$(6) rotamers], 7.72 and 7.88 (4H, 2xd, J=7.1 Hz, Fmoc aromatic C$\underline{H}$); m/z (FAB) 541 (M+Na$^+$, 2%), 519 (M+H$^+$, 5), 179 (33), 103 (17), 85 (100), 77(18), 59 (43), 47(45); $[\alpha]_D^{23}$ +4.26 (c=0.61, DMF).

N-(N-Fluoren-9-ylmeoxycarbonylglycyl)-4thymin-1-yl)proline penfafluonophenyt ester (6a), (6b) and (6c)

A suspension of the Fmoc-dipeptide (5a, 5b or 5c) (1.0 mmol), pentafluorophenol (1.1 mmol) and dicyclohexylcarbodiimide (1.1 mmol) in dichloromethane (5 ml) was stirred at room temperature for 2–3 h. The precipitated dicyclohexylurea was filtered off and washed with dichloromethane. Evaporation of the filtrate followed by column chromatography (SiO$_2$, ethyl acetate) gave the product as white foam which in most cases could be made crystalline by trituration with ether-petroleum ether, filtered and air dried.

N-(N-Fluoren-9-ylmethoxycarbonylglycyl)-cis-4-(thymin-1-yl)-L-proline pentafluorophenyl ester (6a) was obtained from (5a) as a white solid (0.574 g, 84%), m.p. 124–126° C., $\delta_H$ (200 MHz; CDCl$_3$) 1.94 (3H, s, thymine C$\underline{H}_3$), 2.26–2.42 and 2.85–3.00 [2H, m, C$\underline{H}_2$(3')], 3.66–3.75 and 3.95–4.26 [m, unresolved C$\underline{H}_2$(5'), Gly C$\underline{H}_2$, Fmoc aliphatic C$\underline{H}$], 4.38–4.42 (2H, d, J=7.1 Hz, Fmoc C$\underline{H}_2$), 4.85–4.93 [1H, m, C$\underline{H}$(2'), 5.34–5.42 [1H, m, C$\underline{H}$(4')], 5.8–5.82 (1H, br t, Gly N$\underline{H}$), 7.10 [1H, s, C$\underline{H}$(6)], 7.31–7.44, 7.60–7.63 and 7.75–7.79 (8H, m, Fmoc aromatic C$\underline{H}$), 9.50 (1H, s, thymine N$\underline{H}$); $\delta_F$ (235.35 MHz; CDCl$_3$) −162.0 (dd, J=18.1, 21.4 Hz) and −161.2 (t, J=19.6 Hz) (m-F major and minor rotamers), −157.0 (t, J=21.8 Hz) and −156.2 (t, J=21.7 Hz) (p-F major and minor rotamers), −153.1 (d, J==18.5 Hz) and −152.8 (d, J=17.7 Hz) (o-F minor and major rotamers). The ratio of major:minor rotamers was ca. 15:1; m/z (ES MS) 685.1 (M+H$^+$, 100%); $\nu_{max}$ (KBr)/cm$^{-1}$ 1801 (C=O), 1675br (C=O); $[\alpha]_D^{23}$ −15.9 (c=0.630, CHCl$_3$);

N-(N-Fluoren-ylmethoxycarbonylglycyl)-trans-4-(thymin-1-yl)-D-proline pentafluorophenyl ester (6b) was obtained from (5b) as a white solid (0.400 g, 58%), m.p. 115–124° C., $\delta_H$ (200 MHz; CDCl$_3$) 1.94 (3H, s, thymine C$\underline{H}_3$), 2.49–2.61 and 2.79–2.95 [2H, m, C$\underline{H}_2$(3')], 3.79–4.13 [4H, m, C$\underline{H}_2$(5') and Gly C$\underline{H}$], 4.22 (1H, t, J=16.7 Hz, Fmoc aliphatic C$\underline{H}$) 4.37–4.41 (2H, d, J=7.1 Hz, Fmoc C$\underline{H}_2$), 5.04–5.18 [2H, m, C$\underline{H}$(2') and C$\underline{H}$(4')], 5.78–5.82 (1H, br t, Gly N$\underline{H}$), 7.00 and 7.02 [1H, 2xs, C$\underline{H}$(6) rotamers], 7.27–7.44, 7.58–7.61 and 7.74–7.78 (8H, m, Fmoc aromatic C$\underline{H}$), 9.17 and 9.21 (1H, 2xs, thymine N$\underline{H}$ rotamers); $\delta_F$ (235.35 MHz; CDCl$_3$) −162.1 (t, J=19.3 Hz) and −161.4 (t, J=21.8 Hz) (m-F major and minor rotamers), −157.2 (t, J=22.5 Hz) and −156.3 (t J=19.4 Hz) (p-F major and minor rotamers), −153.3 (d, J=19.5 Hz) and −153.0 (d, J=20.0 Hz) (o-F minor and major rotamers); $\nu_{max}$ (KBr)/cm$^{-1}$ 1797 (C=O), 1679br (C=O); $[\alpha]_D^{23}$ +30.0 (c=0.73, CHCl$_3$).

N-(N-Fluoren-9-ylmethoxycarbonylglycyl)-cis-4-(thymin-1-yl)-D-proline pentafluorophenyl ester (6c) was obtained from (5c) as a white solid (0.520 g, 76%), m.p. 122–126° C., H (200 MHz; CDCl$_3$) 1.94 (3H, s, thymine C$\underline{H}_3$), 2.26–2.42 and 2.85–3.00 [2H, m, C$\underline{H}$(3')], 3.66–3.75 and 3.95–4.26 [5H, m, C$\underline{H}_2$(5'), Gly C$\underline{H}_2$ and Fmoc aliphatic C$\underline{H}$], 4.38–4.42 (2H, d, J=7.1 Hz, Fmoc C$\underline{H}_2$), 4.85–4.93 [1H, m, C$\underline{H}$(2')], 5.34–5.42 [1H, m, C$\underline{H}$(4')], 5.80–5.82 (1H, brt, Gly N$\underline{H}$), 7.10 [1H, s, C$\underline{H}$(6)], 7.31–7.44, 7.60–7.63 and 7.75–7.79 (8H, m, Fmoc aromatic C$\underline{H}$), 9.50 (1H, s, thymine N$\underline{H}$); $\delta_F$ (235.35 MHz; CDCl$_3$) −162.0 (dd, J=18.1, 21.4 Hz) and −161.2 (t, J=19.6 Hz) (m-F major and minor rotamers), −157.0 (t, J=21.8 Hz) and =156.2 (t, J=21.7 Hz) (p-F major and minor rotamers), −153.1 (d, J=18.5 Hz) and −152.8 (d, J=17.7 Hz) (o-F minor and major rotamers). The ratio of major minor rotamers was ca. 15:1; $\nu_{max}$ (KBr)/cm$^{-1}$ 1800 (C=O), 1683br (C=O); $[\alpha]_D^{23}$ +16.3 (c=0.645, CHCl$_3$).

Procedure for Deprotecton of Diphenylmethyl Esters and Synthesis of Fmoc-dipeptide Pentaflurophenyl Esters (10, 13 and 16)

The Fmoc dipeptide diphenylmethyl ester (9,12 or 15) was treated with trifluoroacetic acid (ca. 5–10 ml/mmol) containing anisole (50 μL/ml TFA) for 2–3 h. The volatiles were evaporated under reduced pressure and the residue was triturated and washed with diethyl ether. The free acid was obtained as a white solid in nearly quantitative yield after drying over NaOH pellets in vacuo. This was dissolved in 1:1 DMF:dichloromethane (5 ml/mmol) and pentafluorophenol (1.5 eq.) and DCCl (1.5 eq.) was added with stirring at room temperature. The reaction mixture was stirred at room temperature for 1–3 h (tlc). The DCU precipitate was filtered off and washed with dichloromethane. The combined organic phase was washed with water, dried (MgSO$_4$) and evaporated under reduced pressure. The residue was triturated with diethyl ether:petroleum ether 40–60° C. or re-precipitated from suitable solvents to give the product which contained a trace of DCU (~10%) as the only impurity according to $^1$H nmr but was pure enough for solid phase synthesis.

N-(N-Fluoren-9-ylmethoxycarbonylglycyl)-cis-4-(N$_6$-benzoyladenin-9-yl)-D-proline pentafluorophenyl ester (10) was obtained as a white solid (83%, starting from 0.5 mmol of 9), m.p. 125–130° C., $\epsilon_H$ (200 MHz; CDCl$_3$) 2.86–3.02 and 3.10–3.24 12H, m, C$\underline{H}_2$(3')], 3.98–4.42 [7H, m, C$\underline{H}_2$(5'), Gly C$\underline{H}_2$ and Fmoc aliphatic C$\underline{H}$ and C$\underline{H}_2$], 4.97–5.06 [1H, t, J=8.5 Hz, C$\underline{H}$(2')], 5.31–5.42 [1H, m, C$\underline{H}$(4')], 5.70–5.74 (1H, br t, J=3.8 Hz, Gly N$\underline{H}$), 7.27–7.79 (11H, m, Fmoc aromatic C$\underline{H}$ and benzoyl m- and p-C$\underline{H}$), 8.02–8.06 (2H, d, J=6.7 Hz, benzoyl o-C$\underline{H}$), 8.13 [1H, s, C$\underline{H}$(8)], 8.80 [1H, s, C$\underline{H}$(2)], 9.00 (1H, br s, benzamide N$\underline{H}$); m/z (ES MS) 798 (M+H$^+$, 100%); $\nu_{max}$ (KBr)/cm$^{-1}$ 1798 (C=O), 1671br (C=O).

N-(N-Fluoren-9-ylmethoxycarbonylglycyl)-cis-4-(N$_4$-benzoyicytosin-1-yl)-D-proline pentafluorophenyl ester (13) was obtained as a white solid (81%, starting from 0.17 mmol of 12), m.p. 133–137° C., $\delta_H$ (200 MHz; CDCl$_3$) 2.46–2.60 and 290–3.12 [2H, m, C$\underline{H}_2$(3'), 3.80–4.43 [7H, m, C$\underline{H}_2$(5'), Gly C$\underline{H}_2$ and Fmoc aliphatic C$\underline{H}$ and C$\underline{H}_3$], 4.93–5.01 [1H, t, J=7.7 Hz, C$\underline{H}$(2')], 5.41–5.49 [1H, m, C$\underline{H}$(4')], 5.72–5.78 (1H, br t, J=4.5 Hz, Gly N$\underline{H}$), 7.27–7.79 [m, C$\underline{H}$(6), C$\underline{H}$(5), Fmoc aromatic C$\underline{H}$ and benzoyl C$\underline{H}$], 7.90 (1H, br s, benzamide N$\underline{H}$); $\delta_F$ (235.35 MHz; CDCl$_3$) –162.0 (t, J=21.1 Hz) and –161.3 (t, J=19.1 Hz) (m-F major and minor rotamers), –157.2 (t, J=19.4 Hz) and –156.4 (t) (p-F major and minor rotamers), –152.6 (d, J=20.0 Hz) (o-F); mnz (ES MS) 774 (M+H$^+$, 100%); $\nu_{max}$ (KBr)/cm$^{-1}$ 1797 (C=O), 1669 (C=O).

N-(N-Fluoren-9-ylmethoxycarbonylglycyl)-cis-4-N$_2$-isobutyrylguanin-9-yl)-D-proline pentafluorophenyl ester (16) was obtained as a white solid (63%, starting from 0.16 mmol of 15), m.p. 146–150° C., $\delta_H$ (200 MHz; CDCl$_3$) 1.22–1.27 [6H, 2xd, J=6.9 Hz, (C$\underline{H}_3$)$_2$CH], 2.60–2.82 and 2.97–3.12 [3H, m C$\underline{H}_2$(3') and (CH$_3$)$_2$C$\underline{H}$], 4.08–4.30 15H, m, C$\underline{H}_2$(5'), Gly C$\underline{H}_2$ and Fmoc aliphatic C$\underline{H}$], 4.37–441 (2H, d, J=7.2 Hz, Fmoc C$\underline{H}_2$), 4.85–4.94 [1H, t, J=8.3 Hz, C$\underline{H}$(2')], 4.99–5.06 [1H, m, C$\underline{H}$(4')], 5.79–5.84 (1H, br t, J=4.5 Hz, Gly N$\underline{H}$), 7.27–7.44 (4H, m, Fmoc aromatic C$\underline{H}$), 7.56–7.60 (2H, d, J=7.4 Hz, Fmoc aromatic C$\underline{H}$), 7.67 [1H, s, C$\underline{H}$(8)], 7.74–7.78 (2H, d, J=7.4 Hz, Fmoc aromatic C$\underline{H}$), 8.95 (1H, s, isobutyramide N$\underline{H}$); m/z (ES MS) 780 (M+H$^+$, 100%); $\nu_{max}$ (KBr)/cm$^{-1}$ 1798 (C=O), 1680br (C=O).

Novasyn™ TGR resin (~0.23 mmol free N$\underline{H}_2$ group/g) (Fmoc/O$^t$Bu strategy), were obtained from Calbiochem-Novabiochem Ltd. The protected amino acids and derivatives and the coupling reagents (HBTU, PyBrop) were also obtained from the same source. Trifluoroacetic acid (98%) was obtained from Avocado Research Chemicals Ltd. All other reagents were obtained at highest purity grade available either from Aldrich Chemical Company Ltd. or Lancaster Synthesis Ltd. and were used as received. Reagents for the Kaiser test were prepared according to the literature.[23]

DMF was peptide synthesis grade obtained from Rathburn Chemicals Ltd. and used without further purification. All other solvents used for the synthesis and purification were hplc grade solvents obtained from Rathbum. Deionised water was obtained from an Elga Maxima Ultra-Pure water purification system.

Samples for reverse phase hplc analysis were dissolved in a suitable aqueous solvent and filtered through a teflon filter (0.47$\mu$ pore size, Anachem Ltd.). Hplc was performed on a Waters 990+ system with a diode array detector. A Waters $\mu$Bondapak C-18 semi-preparative reverse phase hplc column (0.78×30 cm, P/N 84176) was used for both analysis and preparative purposes. Peak monitoring and data analysis were performed on Waters 990 software running on a NEC IBM-PC/AT compatible computer with 80286/80287 microprocessors. The samples were recovered from hplc fractions by freeze drying on a VirTis Freezemobile 5SL freeze drier. Electrospray mass spectra of the peptide nucleic acids were recorded by on a VG Biotech-BioQ or VG Biotech Platform mass spectrometers.

Small Scale Solid Phase Synthesis of Peptide Nucleic Acids Using Fmoc/O$^t$Bu-fragment Coupling Strategy In a polyethylene syringe (1 ml) equipped with a removable stainless steel needle fitted with a glass wool plug at the junction was placed the Novasyn TGR resin [preloaded with Fmoc-Lys(Boc)-OH 0.23 mmol/g; 10–25 mg, ca. 2.55 $\mu$mol]. The needle was then inserted through a rubber septum fitted to a Büchner flask. Washing was done by adding solvent from the top of the syringe with the plunger removed and sucking into the receiver flask by a water aspirator. For the deprotection, coupling and capping stages, the plunger was re-attached and the reagent was taken up through the needle. Deprotection of the Fmoc group was accomplished by treatment of the Fmoc-pepfide resin with freshly prepared 20% piperidine in DMF (1.0 ml on a 5$\mu$mol scale synthesis) for 20 min with occasional agitation. After the specified period of time the reagent was ejected by depressing the plunger and washing carried out as described above. The solution from the deprotection stage containing the dibenzofulvene-piperidine adduct was collected and the OD$_{264}$ measured to assess the efficiency of the previous coupling stage. The resin had to be washed exhaustively to ensure complete removal of the piperidine. The coupling was carried out similarly using typically 4 equivalents of the Fmoc-dipeptide pentafluorophenyl ester and 4 equivalents of HOBt.H$_2$O in DMF with a final concentration of the pentafluorophenyl ester at approximately 0.1 M. Generally the coupling was completed within 3 h and no second coupling was required. In cases where incomplete coupling was suspected, the peptide resin was treated with 5% Ac$_2$O in DMF (1 ml for a 5 $\mu$mol scale synthesis) for 30 min at room temperature to prevent the formation of deletion sequences. The acetylating mixture was ejected and the reaction vessel flushed with DMF 3 times before the deprotection-coupling-capping steps repeated until the last peptide fragment had been added. The N-terminal Fmoc group was removed by 20% piperidine in DMF and the resin was washed with DMF. If the sequence contained only thymine or if the exocyclic amino protecting groups were to be retained, the cleavage of the peptide nucleic acid from the resin with trifluoroacetic acid was performed directly. However, when a fully deprotected peptide nucleic acid containing adenine, cytosine and/or guanine was required, the resin-bound peptide was capped with a Boc group prior to the cleavage as described below.

Deprotection of Exocyclic Amino Protecting Groups on Nucleobases (A, C and/or G containing sequences only) via a Temporary Boc-protection The resin-bound peptide containing a free amino terminus (5 μmol scale synthesis) was treated with a solution of di-t-butyl dicarbonate (50 μL, 22 μmol) and DIEA (35 μL, 20 μmol) in DMF (150 μL) at room temperature. Kaiser testing indicated complete reaction after 3 h. The resin was washed several times with DMF and then the exocyclic amino protecting groups were removed by treatment with 1:1 mixture of ethylenediamine and 95% ethanol (200 μL) at room temperature overnight. For cytosine containing sequences, the peptide nucleic acids were treated with 1:1 concentrated aqueous ammonia-dioxane at 55° C. for 16 h instead of ethylenediamine-ethanol to avoid the transamination reaction at cytosine residues. The resin-bound deprotected peptide nucleic acid from either method was washed with DMF then methanol and air dried.

Hybridisation Studies with Peptide Nucleic Acids

Sterile deionised water was used for all experiments involving oligonucleotides and nucleopeptides. Poly(2'-deoxyadenylic acid) [poly(dA)] (sodium salt, average Mr 8.9×10⁴) was obtained from Pharmacia Biotech. Polyadenylic acid [poly(rA)] (potassium salt, average Mr 7×10⁶) was obtained from Fluka Chemicals Ltd. Oligonucleotides were synthesised by the phosphoramidite method on Applied Biosystems DNA synthesisers, model 380B or model 394. The exocyclic amino protecting groups were removed by heating with concentrated aqueous ammonia solution at 55° C. overnight and the solvent was evaporated under vacuum at 40° C. on a Savant SpeedVac vacuum concentrator (Savant Instruments). The oligonucleotides were purified by ethanol precipitation in the presence of ammonium acetate, reverse phase hplc (0.1 M triethylammonium acetate buffer-acetonitrile gradient system) or by an Oligonudeotide Purification Cartridge (OPC column, Applied Biosystems Inc.) as appropriate and were stored as a concentrated aqueous solution at neutral pH at −20° C.

The concentration of oligonucleotide, nucleic acid and nucleopeptide solutions was determined from the absorbance at 260 nm (OD260). The following molar extinction coefficients (e) were used without compensation for the hypochromic effect due to the formation of ordered secondary structure of single-stranded nucleic acids: A, 15.4 ml/mmol.cm; T, 8.8 ml/mmol.cm. The same values were also used for nucleopeptides. Temperature dependent UV measurements All the $T_m$ measurements were carried out on a Varian CARY 13 UV spectrophotometer equipped with a temperature control system. The machine was controlled by a CARY 13 software running on an IBM PS/2 system model 30/286. The sample for $T_m$ measurement was prepared by mixing calculated amounts of stock oligonucleotide and nudeopeptide solutions together and the calculated amounts of NaCl and sodium phosphate buffer (pH 7.0) were then added as stock solutions and the final volumes were adjusted to 3.0 ml by addition of water. The samples were transferred to a 10 mm quartz cell with teflon stopper and equilibrated at the starting temperature for at least 30 min. The OD260 was recorded in steps from 5–95° C. (heater temperature) with a temperature increment of 0.25–0.5° C./min. The results were normalised by dividing the absorbance at each temperature by the initial absorbance. Analysis of the data was performed on a KaleidaGraph software 2.1.3 (Abelbeck Software) running on a Macintosh LC III computer. The OD260 was normalised by dividing with the initial OD260. The melting temperatures were determined from the maxdma of the first derivative plots of the normalised OD260 against temperature. Percent hyperchromicity was calculated from the ratio of the OD260 at the end of experiment to the initial OD260.

UV-Titration Experiment

The UV titration experiment was performed on a Pye Unicam SP8-100 UV spectrophotometer at room temperature. To a solution containing the cis-D decathymine peptide nucleic acid (OD260=0.145; 16.5 mM dT nucleotide) and 10 mM sodium phosphate buffer pH 7.0 (2.0 ml) was added a 10 ml aliquot of a concentrated stock solution of poly(rA) (OD260=4.34; 0.28 mM dA nucleotide) in 10 mM sodium phosphate buffer pH 7.0. The absorbance was read against a blank (10 mM sodium phosphate) and more poly(rA) aliquots were added until a total volume of 500 ml had been added. The ratio of the observed OD260 and the calculated OD260 (equation 2) were plotted against the mole ratio of T:A nucleotide (equation 3) and the stoichiometry was determined from the inflection point.

$$\text{calcd. } OD260 = [OD260(T) \times V_T + OD260(A) \times V_A]/[V_T + V_A] \quad (2)$$
$$= [0.145 \times 2 + 4.34 \times V_A(\text{ml})]/2 + V(\text{ml})]$$

$$\text{ratio of } T:A = [\varepsilon_A \times OD260(T) \times V_T]/[\varepsilon_T \times OD260(A) \times V_A] \quad (3)$$
$$= [15.4 \times 0.145 \times 2]/[8.8 \times 4.34 \times V_A(\text{ml})]$$

N-(N-Fluoren-9-ylmethoxycarbonyl-O-t-butyl-L-seryl)-cis-4-(benzoylthymin-l-yl)-D-proline diphenylmethyl ester N-Boc-D-Pro(cis-4-BzTh)-ODpm (350 mg, 0.58 mmol) was dissolved in acetonitrile (5 mL). p-Toluenesulfonic acid monohydrate (552 mg, 2.9 mmol) was added and the solution was stirred at room temperature for 1.5 h, after which tlc indicated complete deprotection of the N-Boc group. Diisopropylethylamine (515 ml, excess) and DMF (5 ml) were added and the reaction stirred under argon. In a separate reaction vessel, a mixture of Fmoc-L-Ser(O$^t$Bu)-OH (268 mg, 0.70 mmol) HOBt H$_2$O (118 mg, 0.77 mmol) and DCCl (160 mg, 0.78 mmol) in DMF (2 ml) was stirred at room temperature. After 2 hours, a white precipitate of dicyclohexylurea formed which was removed by filtration and the filtrate transferred to the first reaction vessel. The reaction mixture was stirred at room temperature for a further 3 h then diluted with dichloromethane (50 ml) followed by washing with saturated aqueous NaHCO$_3$ and water. The organic phase was dried (MgSO$_4$) and the solvent removed under reduced pressure to give the crude product as an oil which was purified by column chromatography (SiO$_2$; dichloromethane : acetone 20: 1). The product (R$_f$=0.43) was obtained as a white foam (455 mg, 89%), δ$_H$ (200 MHz, CDCl$_3$) 1.15 (9H, s, $^t$Bu), 1.81 (3H, s, thymine CH$_3$), 2.01–2.15 and 2.41–2.83 [2H 2xm, CH$_2$(3')], 3.45–3.54(1H, m) 3.63–3.71 (1H, m) 3,80–3.89 (1H, m) [CH$_2$(5') and Ser CH$_a$H$_b$], 4.19–4.54(5H, m, unresolved Fmoc aliphatic CH, CH$_2$ and Ser CH$_a$H$_b$), 4.71–4.79 [2H, m, CH(2') and Ser CH], 5.18–5.30 [CH(4')], 5.73–5.77 (1H, d J=8.2 Hz, peptide NH), 6.90 (1H, s, CHPh$_2$), 7.18 [1H, s, CH(6)], 7.22–7.66 (m, phenyl, Fmoc and benzoyl aromatic CH), 7.90–7.94 and 8.04–8.08 (2×2H, 2xd, Fmoc aromatic CH); d$_c$ (50.28 MHz; CDCl$_3$) 12.3 (thymine CH$_3$), 27.3 ($^t$Bu CH$_3$), 33.1 [CH$_2$(3')], 47.0 (Fmoc aliphatic CH), 49.5 [CH$_2$ (5')]. 52.5 and 52.9 [Ser C$_a$H and CH(4')], 57.5 [CH(2')], 63.3 and 64.0 (Ser CH$_2$ rotamers), 67.3 (Fmoc CH$_2$), 73.9 ($^t$Bu C), 78.5 (CHPh$_2$), 112.0[C(5)], 120.2 (Fmoc aromatic CH), 125.2–131.7 (aromatic CH), 135.4 and 136.0[CH(6) and benzoyl CH], 139.5 and 139.8 (aromatic C rotamers), 141.5, 143.9 and 144.1 (Fmoc aromatic C), 150.1 [C(2)], 156.2 (Fmoc CO), 162.7 [C(4)], 169.1 (benzoyl CO), 170.5 (peptide CO), 170.8 (ester CO); M/z (APCl+) 931 (M+C$_4$H$_8^+$, 90%) 876 (M+H$^+$, 88), 654, 587, 550, 503, 409, 165, 105 (PhCO$^+$, 100).

NN-Fluoren-9-ymethoxycarbonyl-O-t-buty-D-seryl)-cis-4-(benzoylthymin-1-y-D-proline diphenylmethyl ester was obtained in analogous manner to the L-Ser-D-Pro diastereomer as a white foam [78%, starting from 1.08 mmol of Boc-protected proline derivative and 1.20 mmol of Fmoc-D-Ser(OtBu)-OH] after column chromatography: $\delta_H$ (200 MHz; $CDCl_3$) 1.18 and 1.21 (9H, 2xs, tBu rotamers), 1.70 and 1.85 (3H, 2xs, thymine $CH_3$ rotamers), 2.00–2.17 and 2.49–2.88 [2H, 2xm, $CH_2(3')$], 3.37–3.3.72 and 3.99–4.56 [m, unresolved $CH_2(5')$, Ser $CH_2$ and Fmoc aliphatic CH, $CH_2$], 4.63–4.84 [2H, m CH(2') and Set CH], 5.21–5.40 [CH(4')], 5.80–5.84 (1H m, peptide NH, 6.96 (1H, m, C $\underline{H}Ph_2$ rotamers), 7.23 [1H, s, CH(6)], 7.25–7.97 (m, phenyl, Fmoc and benzoyl aromatic CH); $d_c$ (50.28 MHz; $CDCl_3$) 12.3 and 12.4 (thymine $CH_3$ rotamers), 27.2 ($^tBu$ $CH_3$), 33.2 [$CH_2(3')$], 47.1 (Fmoc aliphatic CH), 50.2 [$CH_2(5')$], 52.2, 53.0 and 53.7 [Ser CHand CH(4') rotamers], 57.7and 57.9 [CH(2') rotamers], 63.3 (Ser $CH_2$ rotamers), 67.2 (Fmoc $CH_2$), 74.0 and 74.1 (Bu C rotamers), 78.4 and 79.6 ($CHPh_2$ rotamers), 111.8 and 111.9 [C(5) rotamers], 120.2 (Fmoc aromatic CH), 125.4–131.7 (aromatic CH), 135.4 and 136.4 [CH(6) and benzoyl p-CH], 139.3 and 139.9 (aromatic C rotamers), 141.6, 144.0 and 144.1 (Fmoc aromatic C), 150.0 [C(2)], 156.1 (Fmoc CO), 162.7 [C(4)], 169.2 (benzoyl CO), 170.7 (peptide CO), 170.8 (ester CO); m/z ($APCl^+$) 930 ($M+C_4CH_8^+$, 26%) 876 ($M+H^+$, 38), 708, 653, 587, 550, 503, 167 ($Ph_2CH^+$, 100).

General procedure for deprotection of the diphenylmethyl ester in N-(N-Fluoren-9-ylmethoxycarbonyl-O-t-butylseryo-cis-4-(benzoylthymin-1-yl)-D-proline diphenylmethyl ester The protected dipeptide was treated with a mixture of saturated HCl in dioxane (ca. 5.1 M) and dichloromethane (2:1 v/v) (ca 5 ml/mmol) at room temperature and the progress of the reaction was monitored by tlc. Complete cleavage of the Dpm ester was observed after 6–12h. The reaction mixture was then diluted with dichloromethane and washed with half-saturated aq. $Na_2HPO_4$ and water. Evaporation followed by trituration with ether/light petroleum gave the product as a white solid.

N-(N-Fluoren-9-ylmethoxycarbonyl-O-t-butyl-L-seryl)-cis-4-(benzoylthymin-1-yl)-D-proline was obtained as a white solid [93%, starting from 0.66 mmol of Fmoc-L-Ser($O^tBu$)-D-Pro(cis-4-BzT)-Opm]. $^1H$ nmr revealed the presence of impurities, however, the crude product was used for the next step without further purification.

N-(N-Fluoren-9-ylmethoxycarbonyl-O-t-butyi-D-seryl)-cis-4-(benzoylthymin-1-yl)-D-proline was obtained as a write solid [87%, starting from 1.46 mmol of Fmoc-D-Ser($O^tBu$)-D-Pro(cis-4-BzT)-ODpm]. $^1H$ NMR revealed the presence of impurities, however, the crude product was used for the next step without further purification.

General procedure for synthesis of NN-Fluoren-9-ylmethoxycarbonyl-O-t-butylseryl)-cis-4-(benzoylthymin-1-yl)proline pentafluorophenyl ester A mixture of the N-Fmoc-dipepfide, pentafluorophenol (1.1 eq) and DCCl (1.1 eq) in dichloromethane was stirred at room temperature for 2–3 hr. The precipitated dicyclohexylurea was filtered off, the solvent removed under reduced pressure and the residue purified by column chromatography ($SiO_2$, dichloromethane:acetone or EtOAc).

N-(N-Fluoren-9-ylmethoxycarbonyl-O-t-butyl-L-seryl)-cis-4-(benzoylthymin-l-yl)-D-proline was obtained as a white solid [50%, starting from 1.46 mmol of Fmoc-L-Ser($O^tBu$)-D-Pro(cis-4-BzT)-ODpm] $\delta_H$ (200 MHz; $CDCl_3$) 1.15 (9H, s, $^tBu$), 1.97 (3H, s, thymine $CH_3$), 2.30–2.44 and 2.88–3.04 [2H, 2xm, $CH_2(3')$], 3.45–3.55 (1H, m) 3.59–3.69 (1H, m 3.96 4.05 (1H, m) [$CH_2(5')$ and Ser C $\underline{H}_a H_b$], 4.15–4.27, 4.35–4.39, 4.43–4.56, 4.19–4.54 (5H, m, unresolved Fmoc aliphatic CH, $CH_2$ and Ser $CH_a\underline{H}_b$) 4.67–4.88 [2H, m, CH(2') and Ser $C_aH$], 5.28–5.35 [CH(4')], 5.53–5.57 (1H d J=8.2 Hz, peptide NH), 7.30–7.58 [m, CH(6), phenyl, Fmoc and benzoyl aromatic CH], 7.63–7.70 (2H, m, Bz o-CH), 7.74–7.78 and 7.90–7.94 (2×2H, 2xd, Fmoc aromatic CH); m/z ($APCl^+$) 876 ($M+H^+$, 100), 819 (71), 771, 715, 690, 470, 310, 179, 122.

N-(N-Fluoren-9-ylmethoxycarbonyl-O-t-butyl-D-seryl)-cis-4-(benzoylthymin-1-yl)-D-proline was obtained as a white solid [20%, starting from 1.46 mmol of Fmoc-D-Ser($O^tBu$)-D-Pro(cis-4-BzT)-ODpm] $\delta_H$ (200 MMz; $CDCl_3$) 1.17 (9H. s, $^tBu$), 1.97 (3H, s, thymine $CH_3$), 2.26–2.45 and 2.90–3.05 [2H, 2xm. $CH_2(3')$]. 3.49–3.70(2H, m), 4.05–4.39 (m) [$CH_2(5')$], Fmoc aliphatic CH, $CH_2$ and Ser $CH_2$), 4.61–4.72(1H, m Ser $C_aH$), 4.85–4.93 [$_1H$, m, CH(2')], 5.30–5.39 [CH(4')], 5.58–5.62 (1H, d J=8.2 Hz peptide NH), 7.23 [1H, s, CH(6)], 7.31–7.60 (m, phenyl, Fmoc and benzoyl aromatic CH), 7.63–7,71 (2H, m, Bz o-CH), 7.75–7.79 and 7.91–7.95 (2×2H, 2xd, Fmoc aromatic CH)

Solid Phase Synthesis of Chiralpeptidenucleic Acids Containing Seryl-D-proline Backbone Using Fmoc/OBu-fragment Coupling Strategy Synthesis of CPNA containing D-seryl-D-proline backbone was carried out on 5 mmol scales on Novasyn TGR resin [preloaded with Fmoc-Lys(Boc)-OH0.23 mmolg; 10–25 mg, ca. 2.5–5 pmol] using the dipeptide pentafluorophenyl esters in the presence of HOBT in DMF (4 eq each, 3 h, rt) as descnied previously. The coupling reaction was monitored by measurement of the amounts of dibenzofulvene-piperdine adduct released upon deprotection at 300 nm which generally indicated 95–100% efficiency. After the addition of the final residue was completed, the N-terminal Fmoc group was removed by 20% piperidine in DMF and the cPNA was released from the resin by treatment with trfluoroacetic acid containing 5% anisole (ca. 1 ml for a 5 $\mu$mol synthesis) at room temperature for 4–6 h with occasional agitation. After the specified period of time, the cleavage solution was diluted with diethyl ether (ten times the volume) and kept at −20° C. overnight. The suspension was then centrifuged at 13,000 rpm for 5 min. After decanting the supematant, the crude cPNA was washed with ether and the centrifugation-wash process repeated 4–5 times. Finally the crude cPNA was air dried and dissolved in 10% aqueous acetonitrile containing 0.1% trifluoroacetic acid. The crude solution was filtered and analysed or purified by reverse phase hplc. The sample elution was carried out using a gradient of water-acetonitrile containing 0.1% trifluoroacetic acid. The identity of the products were proved by ESI-MS. The yield of the cPNAs as determined by measurement of OD260 were 28 and 16% for LDT 10 and DD-ST 10 respectively.

$^1H$ NMR Experiment $^1H$ NMR study of a mixture of DDST10 and $dA_{10}$ was performed on a Bruker AMX 500 spectrometer (500 MHz). The $^1H$ NMR spectra of DDST10 and $dA_{10}$ were recorded separately (at a concentration of 0.53 mM for the DD-ST10 and 0.67 mM for the $dA_{10}$ in 10% $D_2O$ in $H_2O$). Upon addition of 20 mol % of $dA_{10}$ (as a concentrated aqueous solution) to a solution of 0.53 mM of DD-ST10 in 10% $D_2O$—$H_2O$, an immediate precipitation occurred.

References

1. E Uhlmann and A. Peyman, Chem Rev., 1990, 90(4), 543.
2. a) P. Garner and J. U. Yoo, Tetrahedron Lett., 1993, 34, 1275; b) I. Lewis, Tetrahedron Lett., 1993, 34, 5697; c) A. Lenzi, G. Reginato, M. Taddei and E. Trifilieff, Tetrahedron Lett., 1995, 36, 1717.

3. P. E. Nielsen, M. Egholm, R. H. Berg and O. Buchardt, Science, 1991, 254, 1497.
4. O. Almarsson, T. C. Bruice, J. Kerr and R. N. Zuckennann, Proc. Nati. Acad. Sci. USA, 1993, 90, 7518.
5. P K T Lin and D M Brown, Nucleic Acids Research, 1989, 17, 10373–83.
6. J. Kovacs in The Peptides Vol 2, E. Gross and J. Meienhofer ed., Academic Press, New York, 1980, pp. 486–536.
7. G. B. Fields and R. L. Noble, Int. J. Peptide Protein Res., 1990, 35, 161.
8. T. W. Green and P. G. M. Wuts, Protecting Groups in Organic Synthesis, 2nd edn., John Wiley & Sons, New York, 1991, p. 328.
9. Z. Tozuka & T. Takaya, J. Antibiotics, 1983, 36, 142
10. G. C. Stalakatos, A. Paganon and L. Zervas, J. Chem. Soc. C, 1966,1 1
11. L. Kisfaludy and I. Schon, Synthesis, 1983, 325.
12. M. L. Peterson and R. Vince J. Med. Chem., 1991, 34, 2787.
13. M. T. Chenon, R. J. Pugmire, D. M. Grant, R. P. Panzica and L. B. Townsend, J. Am. Chem. Soc., 1975, 97, 4627.
14. R. R. Chauvette, R. A. Pennington, C. W. Ryan, R. D. E. Cooper, L. Jose, I. G. Wright, E. M. Heyningen, G. W. Huffmann J. Org. Chem., 1971, 36, 1259.
15. D. M. Brown, A. Todd and S. Varadarajan, J. Chem. Soc., 1956, 2384.
16. T. F. Jenny, K C. Schneider and S. A. Benner, Nucleosides & Nucleotides, 1992, 11, 1957.
17. a) E. Atherton and R. C. Sheppard, Solid Phase Peptide Synthesis, A Practical Approach. IRL Press, Oxford, 1989; b) G. B. Fields and R. L. Noble, Int. J. Peptide Protein Res., 1990, 35, 161.
18. a) M. Goodman and K C. Steuben, J. Am. Chem. Soc., 1962, 84, 1279; b) M. Bodanszky, Principles of Peptide Synthesis, Springer-Verlag, Heidwlberg, 1984, p. 174.
19. P. S. Miller, M. P. Reddy, A, Murakami, K R Blake, S.-B. Lin and C. H. Agris, Biochemistry, 1986, 25, 5092.
20. E. P. Stirchak, J. E. Summerton and D. D. Weller, J. Org. Chem., 1987, 62, 4202.
21. D. D. Perrin and W. L. F. Amarego, Purification of Laboratory Chemicals, 3rd ed., Pergamon Press, Oxford, 1988.
22. J. B. Miller, J. Org. Chem., 1959, 24, 560.
23. E. Kaiser, R. L Colescctt, C. D. Bossinger and P. I. Cook, Anal. Biochem., 1970, 34, 595.

Scheme 1

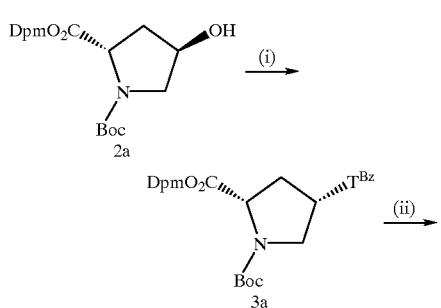

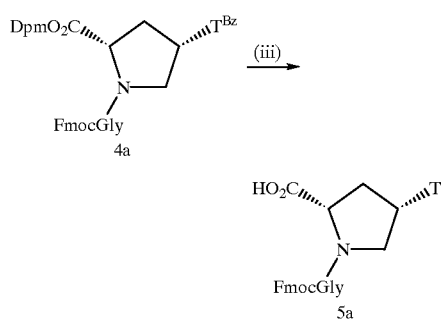

(i) N$_3$-BzT, Ph$_3$P, DEAD in THF, rt, O/N (51%)
(ii) a) THF: satd. HCl in MeOH 1:1, rt, 3h
  b) FmocGlyOPfp, DIEA in dioxane, rt, O/N (99%)
(iii) 10% HBr in HOAc, rt, 1 h (50%)

Scheme 2

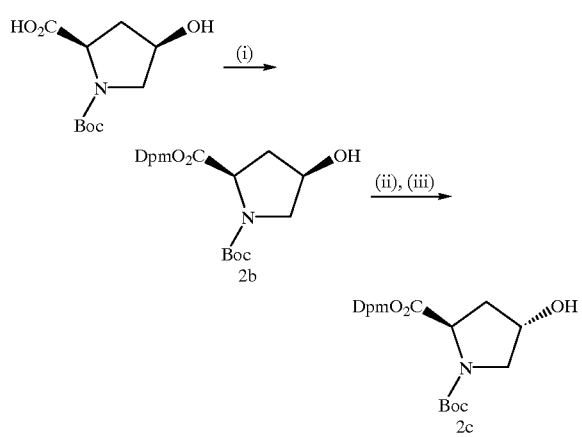

(i) Ph$_2$CH$_2$, EtOAc rt, O/N (90%)
(ii) HCO$_2$H, Ph$_3$P, DEAD in THF, rt, O/N (quant.)
(iii) aq. NH$_3$, MeOH, 1 h (90%)

Scheme 3

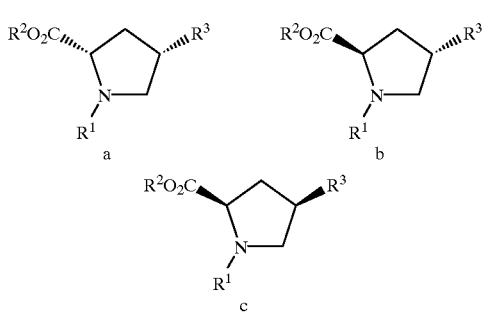

3 R$^1$ = Boc; R$^2$ = Dpm; R$^3$ = T$^{Bz}$
4 R$^1$ = FmocGly; R$^2$ = Dpm; R$^3$ = T$^{Bz}$
5 R$^1$ = FmocGly; R$^2$ = H; R$^3$ = T
6 R$^1$ = FmocGly; R$^2$ = Pfp; R$^3$ = T

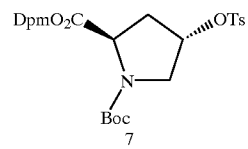

-continued

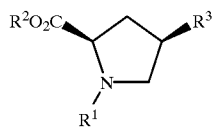

8  $R^1$ = Boc; $R^2$ = Dpm; $R^3$ = $A^{Bz}$
9  $R^1$ = FmocGly; $R^2$ = Dpm; $R^3$ = $A^{Bz}$
10 $R^1$ = FmocGly; $R^2$ = Pfp; $R^3$ = $A^{Bz}$
11 $R^1$ = Boc; $R^2$ = Dpm; $R^3$ = $C^{Bz}$
12 $R^1$ = FmocGly; $R^2$ = Dpm; $R^3$ = $C^{Bz}$
13 $R^1$ = FmocGly; $R^2$ = Pfp; $R^3$ = $C^{Bz}$
14 $R^1$ = Boc; $R^2$ = Dpm; $R^3$ = $G^{Ibu}$
15 $R^1$ = FmocGly; $R^2$ = Dpm; $R^3$ = $G^{Ibu}$
16 $R^1$ = FmocGly; $R^2$ = Pfp; $R^3$ = $G^{Ibu}$ Solid Support: Novasyn TGR Resin (dimethoxybenzhydrylamine-PEG) preloaded with Fmoc-Lys(Boc) (0.2 mmol/g loading)

Synthesis cycle:

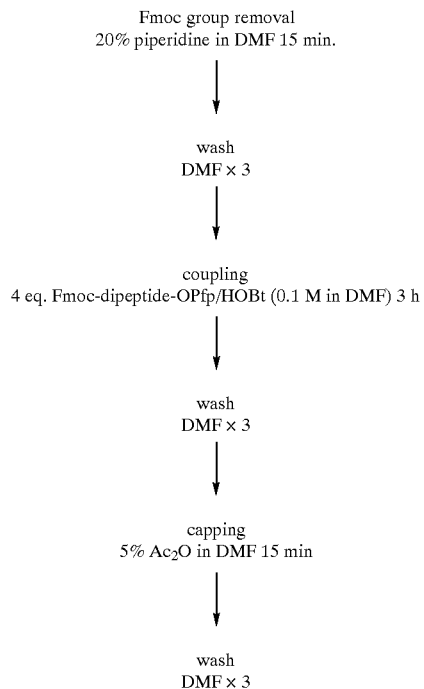

Final deprotection: 20% piperidine in DMF 30 min
Cleavage: 95% TFA 3 h followed by ether precipitation and washing

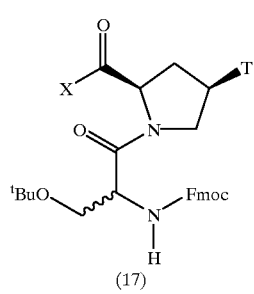

X = ——OH, ——Pfp

-continued

Scheme 4

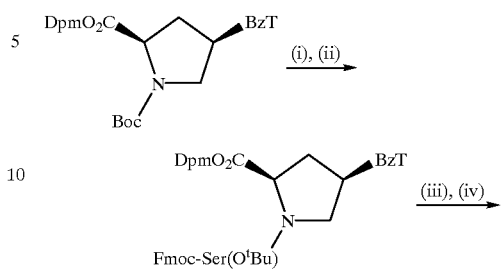

(i) 5 eq. p-TsOH, MeCN, rt, 3 h
(ii) Fmoc-Ser(O$^t$Bu)-OH, DCCI, HOBt, DIEA in MeCN: DMF 1:1 rt, 3h (70–90%)
(iii) 4 N HCl in dioxane: dichloromethane (2:1), rt, O/N
(iv) PfpOH, DCCl in dichloromethane, rt, 2h (20–30%, 2 steps)

TABLE 1

Electrospray mass spectral data of $T_{10}$ chiral peptide nucleic acids. Experimental values are the averaged mass derived from various protonated species in the mass spectra.

| Chiral Peptide Nucleic Acid | $M_r$ (found) | $M_r$ (calcd.) |
| --- | --- | --- |
| H-[Gly-D-Pro(trans-4-T)]$_{10}$-LysNH$_2$ | 2927.53 ± 1.54 | 2927.88 [M] |
|  | 2968.29 ± 0.40 | 2965.97 [M − H + K] |
|  | 3005.07 ± 0.53 | 3004.26 [M − 2H + 2K] |
| H-[Gly-L-Pro(cis-4-T)]$_{10}$-LysNH$_2$ | 2929.02 ± 0.34 | 2927.88 [M] |
|  | 2967.27 ± 0.97 | 2965.97 [M − H + K] |
|  | 3005.88 | 3004.26 [M − 2H + 2K] |
| H-[Gly-D-Pro(cis-4-T)]$_{10}$-LysNH$_2$ | 2929.88 ± 2.81 | 2927.88 [M] |
|  | 2965.52 ± 0.36 | 2965.97 [M − H + K] |
|  | 3004.38 ± 1.39 | 3004.26 [M − 2H + 2K] |
|  | 3043.83 ± 0.66 | 3042.15 [M − 3H + 3K] |

TABLE 2

Melting Temperatures
Melting temperatures $T_m$ (° C.) and % hypochromicity obtained from melting curves (recorded at 260 nm) of the hybrids of the cPNAs with poly(rA), poly(dA) and dA$_{10}$ in 150 mM sodium chloride, 10 mM sodium phosphate pH 7.0. The $T_m$s were determined from the maxima of the first derivative plots of the normalised OD$_{260}$ against temperature. The $T_m$ for the $T_{10}$ oligodeoxyribonucleotide bound to poly(dA) is 27° C. at the same pH and ionic strength.

| cPNA | $T_m$ with poly (rA) (° C.) and % hypochromicity | $T_m$ with poly(dA) (° C.) and % hypochromicity | $T_m$ with dA$_{10}$ (° C.) |
| --- | --- | --- | --- |
| H-[Gly-D-Pro(cis-4-T)]$_{10}$-LysNH$_2$ | 72 (45%) | 70 (28%) | 61 |
| H-[Gly-L-Pro(cis-4-T)]$_{10}$-LysNH$_2$ | 73 (36%) | 69 (40%) | 42 |
| H-[Gly-D-Pro(trans-4-T)]$_{10}$-LysNH$_2$ | No melting observed | No melting observed | No melting observed |

What is claimed is:
1. A compound of formula (I):

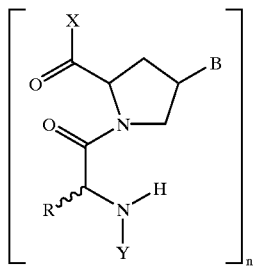

(I)

where n is 1 or 2–200,
B is a protected or unprotected base capable of Watson-Crick or of Hoogsteen pairing,
R is H, $C_1$–$C_{12}$ alkyl, $C_6$–$C_{12}$ aralkyl or $C_6$–$C_{12}$ heteroaryl which may carry one or more substituents,
X is OH or OR' where R' is a protecting group or an activating group or a lipophilic group or an amino acid or amino amide or nucleoside,
Y is H or a protecting group or a lipophilic group or an amino acyl group or nucleoside.

2. A compound as claimed in claim 1, wherein the structure is (II) or (III) where n, B, R, X and Y are as defined in claim 1

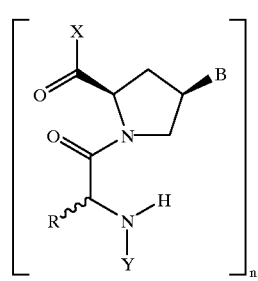

(II)

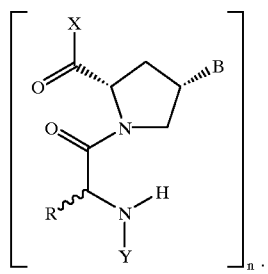

(III)

3. A compound as claimed in claim 1, wherein B is a naturally occurring nucleobase selected from adenine, cytosine, guanine, thymine and uracil.

4. A compound as claimed in claim 1, wherein —CO—CHR—NH— is a residue of naturally occurring amino acid.

5. A compound as claimed in claim 1, wherein R is $CH_2OH$ or $(CH_2)_4NH$, or H.

6. A compound as claimed in claim 1, wherein n is 1,
B is a naturally occurring nucleobase selected from adenine, cytosine, guanine, thymine and uracil,
R is H or $CH_2OH$ or $(CH_2)_4NH_2$,
X is OH or OR',
R' is an activating group for example pentafluorophenyl,
Y is H or a protecting group for example Fmoc.

7. A compound as claimed in claim 1, wherein n is 2–200.

8. A compound as claimed in claim 1, wherein at least one of B, R, X and Y includes a signal moiety.

9. A compound as claimed in claim 1 wherein said substituents are selected from hydroxyl, carboxyl, amine, amide, thiol, thioether or phenol.

10. A compound as claimed in claim 7, wherein n is 5–30.

11. A method of making a pepfide nucleotide analogue of formula (I), comprising the steps of:
a) reacting an N-protected C-protected 4-hydroxy proline with a base selected from $N_3$-protected thymine, $N_6$-protected adenine, $N_4$-protected cytosine, $N_2$-$O_6$-protected guanine and $N_3$-protected uracil,
b) deprotecting the proline amino group of the product of a),
c) reacting the product of b) with an N-protected amino acid,
d) optionally removing protecting groups from the product of c).

12. A method as claimed in claim 1, wherein in a) 4-hydrgxyproline in the form of a N-Boc/Dpm ester is reacted with $N_3$-benzoyl thymine, $N_6$-benzoyl adenine, $N_4$-benzoyl cytosine, $N_2$-benzoyl-$O_6$-(4'-nitrophenylethyl) guanine or $N_3$-benzoyl uracil, and in c) an Fmoc amino acid ester is used.

13. A method as claimed in claim 11, wherein an N-protected C-protected trans-4-hydroxy proline is used in a).

14. A method of converting apeptide nucleotide analogue of formula (1):

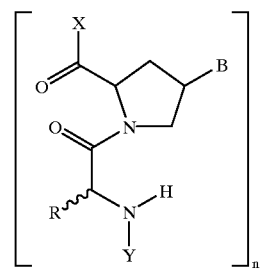

(I)

in which n is 1,
B is a protected or unprotected base capable of Watson-Crick or of Hoogsteen pairing,
R is H, $C_1$–$C_{12}$ alkyl, $C_6$–$C_{12}$ aralkyl or $C_6$–$C_{12}$ heteroaryl which may carry one or more substituents,
X is OH or OR' R' is a protecting group or an activating group or a lipophilic group or an amino acid or amino amide or nucleocide,
Y is H or a protecting group or a lipophilic group or an amino acyl group or nucleocide,
into a peptide oligoncleotide comprising the steps of:
i) providing a support carrying primary amine groups,
ii) coupling an N-protected peptide nucleotide analogue of formula (1) to the support,
iii) removing the N-protecting group,
iv) coupling an N-protected nucleotide analogue of formula (1) to the thus-derivatised support, and
v) repeating steps iii) and iv) one or more times.

15. A method as claimed in claim 14, wherein a pentafluorophenyl ester of the peptide nucleotide analogue is used in step ii) and iii).

16. The method of claim 15 further comprising removing the resulting peptide oligonucleotide from the support.

17. The method of claim 14 further comprising removing the resulting peptide oligonucleotide from the support.

18. The method of claim 14 wherein said substituents are selected from hydroxyl, carboxyl, amine, amide, thiol, thioether or phenol.

* * * * *

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 1
gtagatcact                                                         10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 2
catctagtga                                                         10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 3
agtgatctac                                                         10